(12) United States Patent
Chen et al.

(10) Patent No.: US 9,279,103 B2
(45) Date of Patent: *Mar. 8, 2016

(54) SIMPLIFIED BASIC MEDIA FOR HUMAN PLURIPOTENT CELL CULTURE

(75) Inventors: Guokai Chen, Rockville, MD (US); James A. Thomson, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,354

(22) Filed: Aug. 5, 2011

(65) Prior Publication Data

US 2012/0202291 A1 Aug. 9, 2012

(51) Int. Cl.
- *C12N 5/00* (2006.01)
- *C12N 5/0735* (2010.01)
- *C12N 5/074* (2010.01)

(52) U.S. Cl.
CPC ............ *C12N 5/0606* (2013.01); *C12N 5/0696* (2013.01); *C12N 2500/25* (2013.01); *C12N 2500/38* (2013.01); *C12N 2500/92* (2013.01); *C12N 2500/98* (2013.01); *C12N 2501/115* (2013.01); *C12N 2501/15* (2013.01); *C12N 2501/39* (2013.01); *C12N 2501/727* (2013.01); *C12N 2501/999* (2013.01)

(58) Field of Classification Search
CPC ............................. C12N 5/0606; C12N 5/0696
See application file for complete search history.

(56) References Cited

U.S. PATENT DOCUMENTS

| | | | |
|---|---|---|---|
| 7,439,064 B2 | 10/2008 | Thomson | |
| 7,449,334 B2 | 11/2008 | Thomson | |
| 2010/0221829 A1* | 9/2010 | Amit et al. | 435/366 |

FOREIGN PATENT DOCUMENTS

| | | |
|---|---|---|
| WO | 2007113587 A2 | 10/2007 |
| WO | 2009135206 A1 | 11/2009 |
| WO | 2010048567 A1 | 4/2010 |
| WO | 2011058558 A2 | 5/2011 |

OTHER PUBLICATIONS

Beattie et al. Stem Cells 23:489-495, 2005.*
Yao Shuyuan et al., "Long-term renewal and directed differentiation of human embryonic stem cells in chemically defined conditions", Proc. Natl. Acad. Sci., 2006, vol. 103, No. 18, pp. 6907-6912.
Ludwig, T.E. et al., "Derivation of human embryonic stem cells in defined conditions", Nature Biotechnology, 2006, vol. 24, No. 2, pp. 185-187.
Wells, N. et al., "The geometric control of E14 and R1 mouse embryonic stem cell pluripotency by plasma polymer surface chemical gradients", Biomaterials, 2009, vol. 30, No. 6, pp. 1066-1070.
Johansson, B.M. et al., "Evidence for involvement of activin A and bone morphogenetic protein 4 in mammalian mesoderm and hematopoietic development", Molecular and Cellular Biology, 1995, vol. 15, No. 1, pp. 141-151.
Peiffer, I. et al., "Optimization of physiological xenofree molecularly defined media and matrices to maintain human embryonic stem cell pluripotency", 5, Methods in Molecular Biology, Human Embryonic Stem Cell Protocols, 2009, Springer Protocols, Clifton, N.J.
Ludwig, T.E. et al, "Feeder-independent culture of human embryonic stem cells", Nature Methods, 2006, vol. 3, pp. 637-646.
Thomson, J.A. et al., "Embryonic Stem Cell Lines Derived from Human Blastocysts", Science, 1998, vol. 282, pp. 1145-1147.
Yu, J. et al., "Induced Pluripotent Stem Cell Lines Derived from Human Somatic Cells", Science, 2007, vol. 318., No. 5858, pp. 1917-1920.
Garcia-Gonzalo et al., Albumin-Associated Lipids Regulate Human Embnionic Stem Cell Self-Renewal, PLOS One, 2008, Issue 1, e1384, pp. 1-10.
Rajala et al. "Testing of nine different xeno-free culture media for human embryonic stem cell cultures" Human Reproduction vol. 22, No. 5, pp. 1231-1238, 2007.
Lei et al. "Xeno-free derivation and culture of human embryonic stem cells: current status, problems and challenges" Cell Research (2007) 17:682-688.
L5146 Sigma, Lipid Mixture (Undefined).
Chung et al., "Human embryonic stem cell lines generated without embryo destruction", Cell Stem Cell 2.2 (2008): 113-117.
Ebert et al., "Induced pluripotent stem cells from a spinal muscular atrophy patient", Nature 457.7227 (2009): 277-280.
Harb et al., "The Rho-Rock-Myosin sionaling axis determines cell-cell integrity of self-renewing pluripotent stem cells", PLoS One 3, No. 8 (2008): e3001.
Yu et al., "Human induced pluripotent stem cells free of vector and transgene sequences", Science 324.5928 (2009): 797-801.
Zhi-Xing et al., "Establishment of feeder layer- and serum-free culture system of human embryonic stem cells", CRTER, 2009, 13(45): 8889-8894.
Zhao et al. "Effect of Hypoxia on the Proliferation of Embryonic Stem Cells." (2004). [English abstract only].
Mali, Prashant, et al. "Butyrate Greatly Enhances Derivation of Human Induced Pluripotent Stem Cells by Promoting Epigenetic Remodeling and the Expression of Pluripotency—Associated Genes." Stem cells 28.4 (2010): 713-720.
Chinese Patent Office, Notice for a Reason of Rejection, Application No. 201180038596.9, Feb. 16, 2015, 24 pages. [English translation included].
Japanese Patent Office, Notice for a Reason of Rejection, Application No. 2013-523366, Aug. 19, 2015, 8 pages. [English translation included].

* cited by examiner

*Primary Examiner* — Marcia S Noble
(74) *Attorney, Agent, or Firm* — Quarles & Brady LLP

(57) ABSTRACT

Fully defined media that support pluripotent cell viability, proliferation, cloning, and derivation, as well as methods and compositions including these media are described. Methods for deriving iPS cells from adult individuals under defined, xeno-free conditions are also described.

19 Claims, 16 Drawing Sheets

Figure 1
FIG. 1A
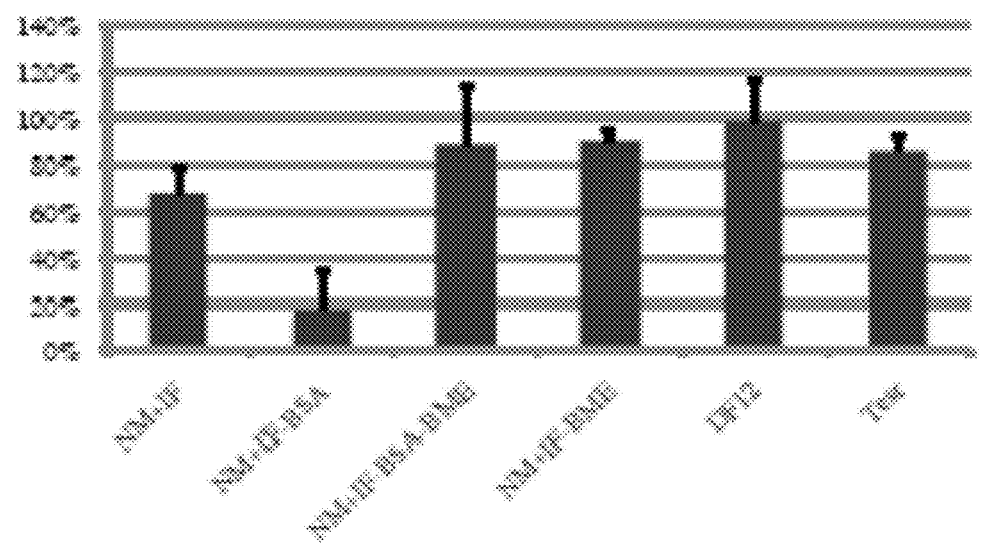
FIG. 1B
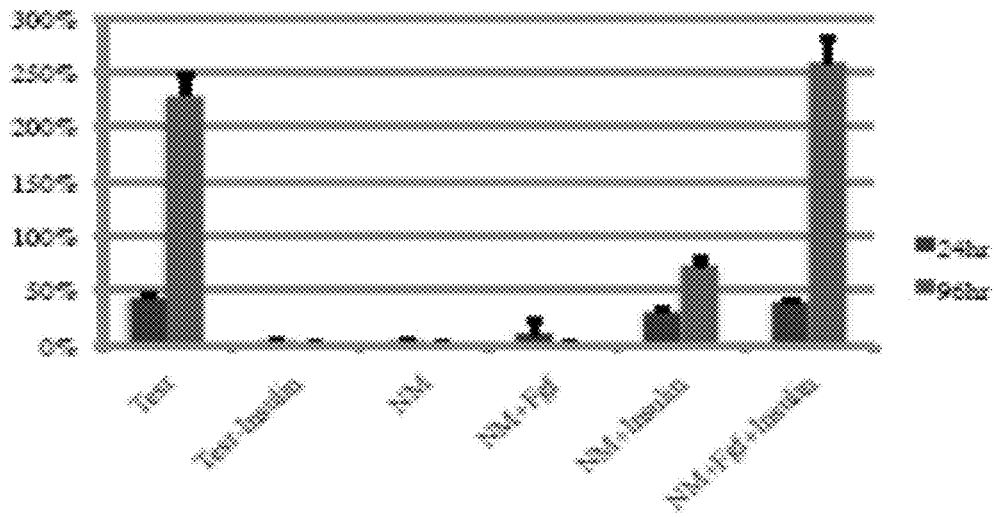

Figure 1
(cont.)
FIG. 1C
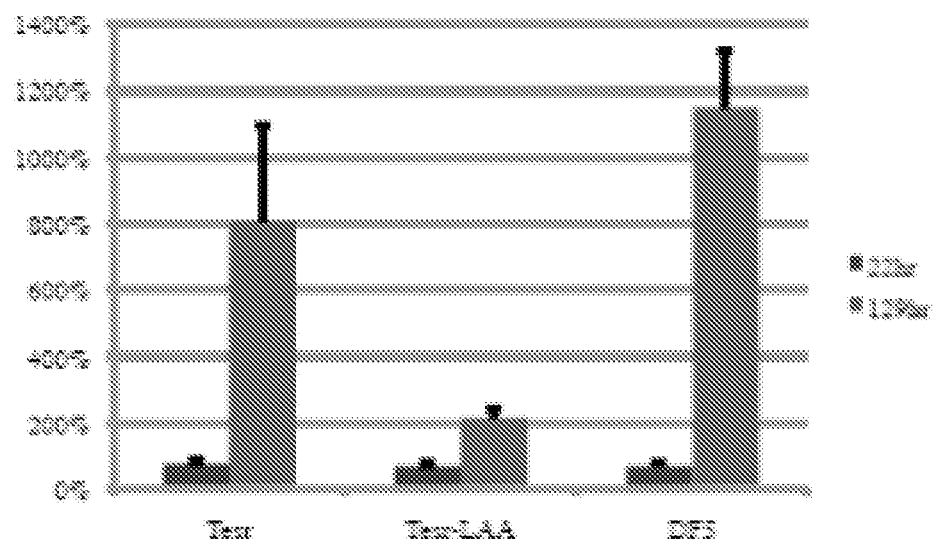
FIG. 1D
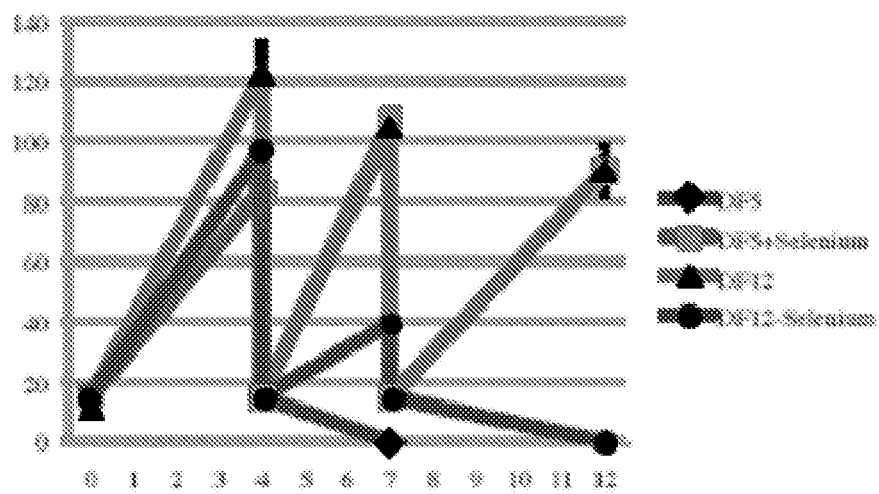

Figure 2
FIG. 2A
TeSR™
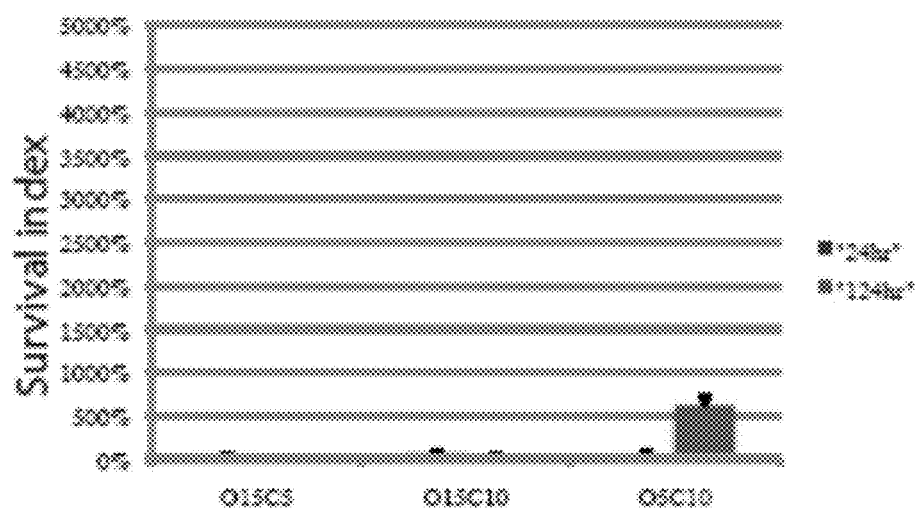
DF5S
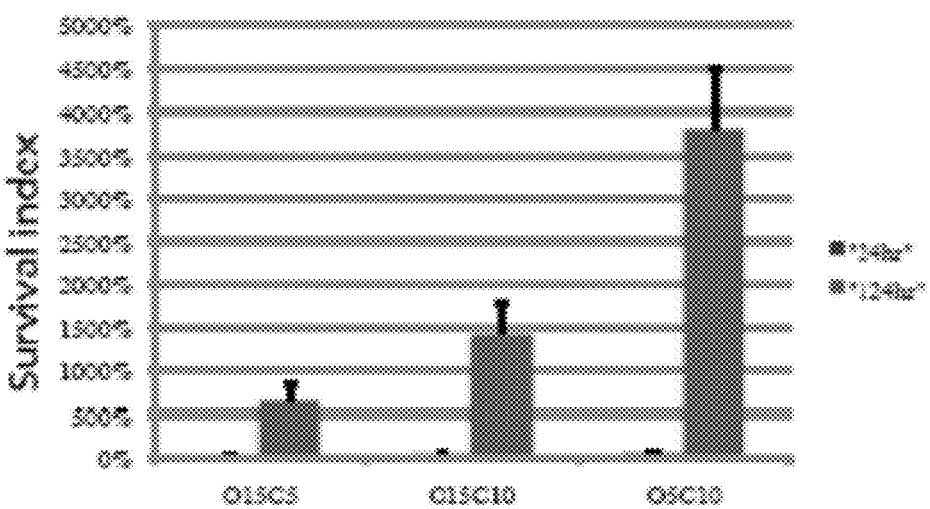

Figure 2
(cont.)
FIG. 2B
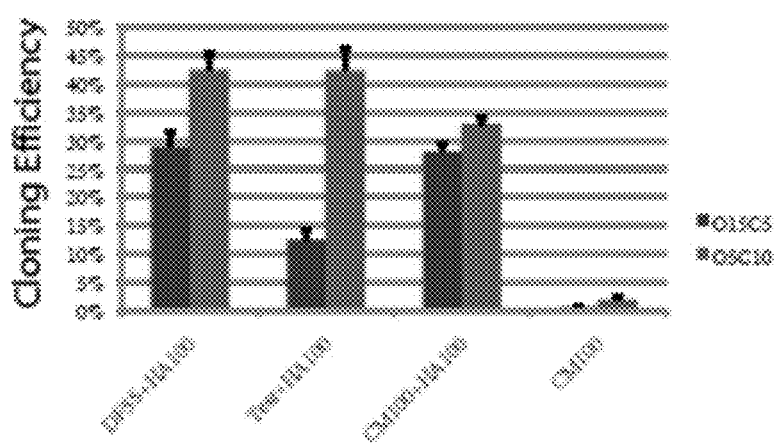
FIG. 2C
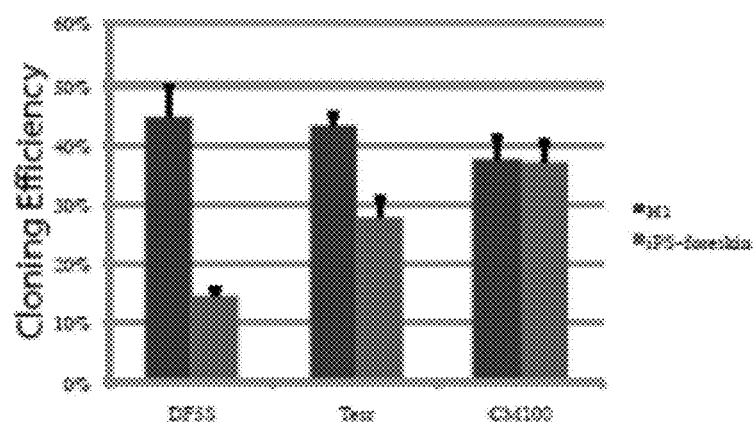
FIG. 2D
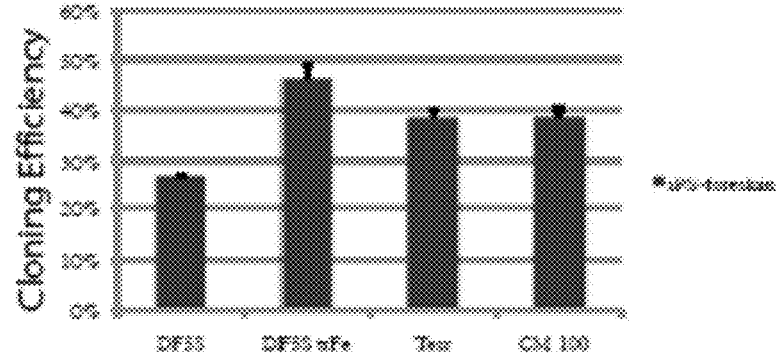

Figure 2
(cont.)
FIG. 2E
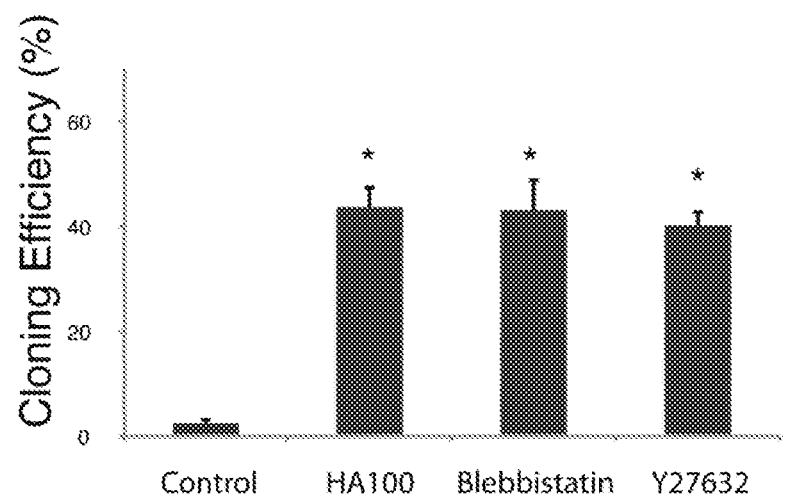
FIG. 2F
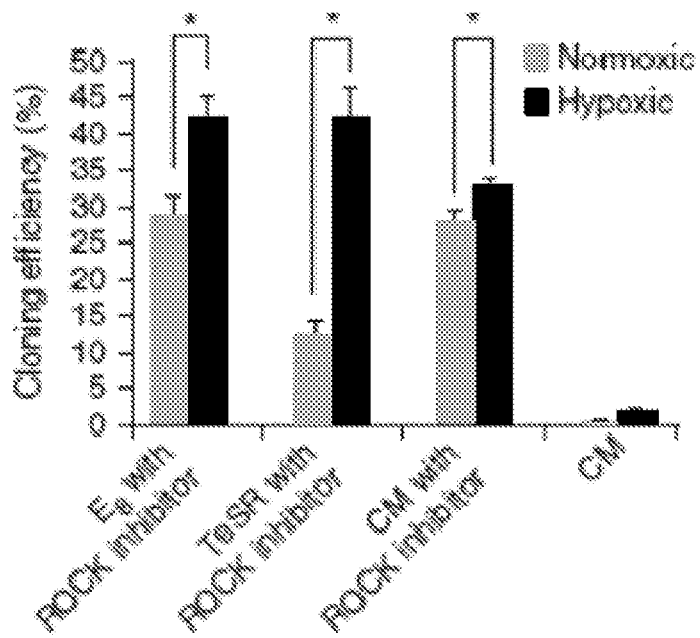

Figure 3
(cont.)
FIG. 3A
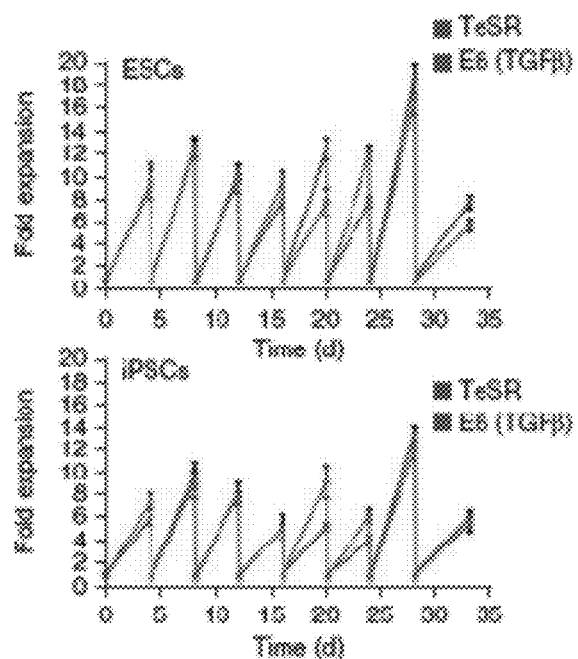
FIG. 3B
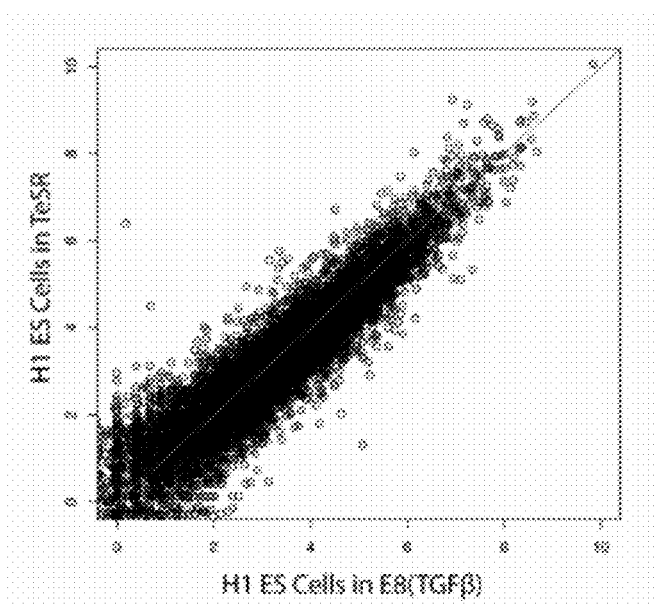

Figure 4
FIG. 4A
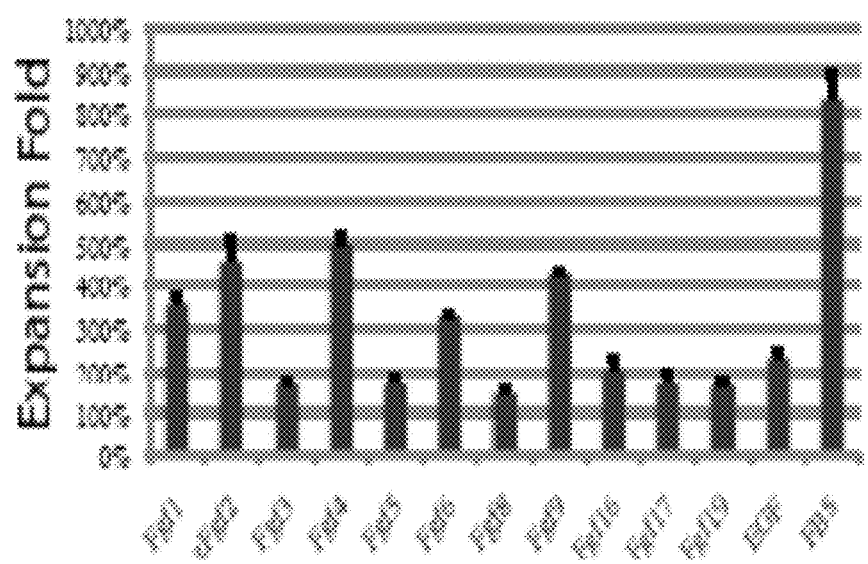
FIG. 4B
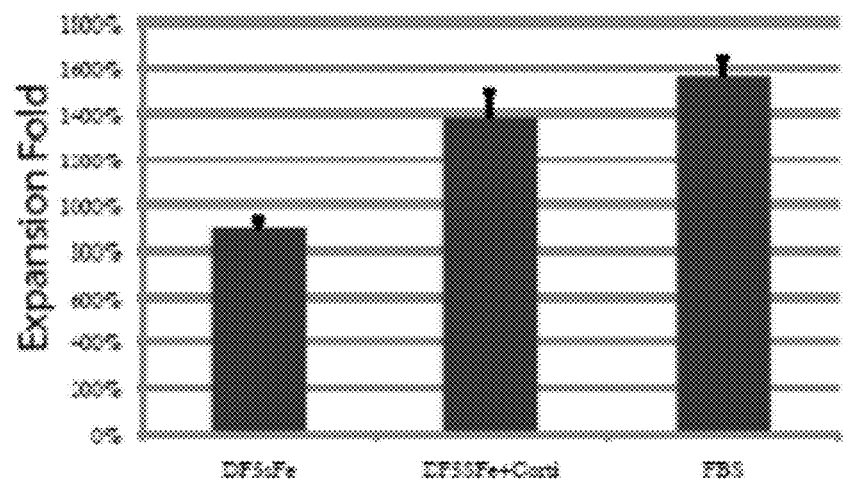

Figure 4
(cont.)
FIG. 4E
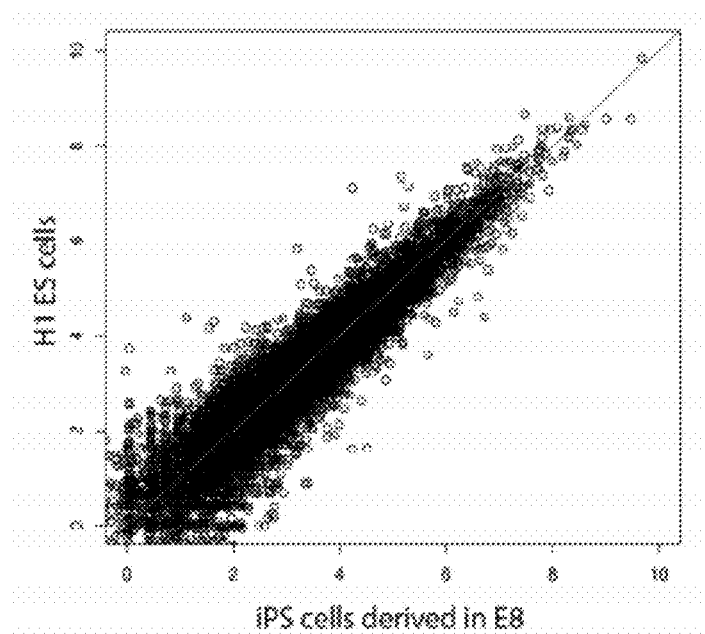
FIG. 4F
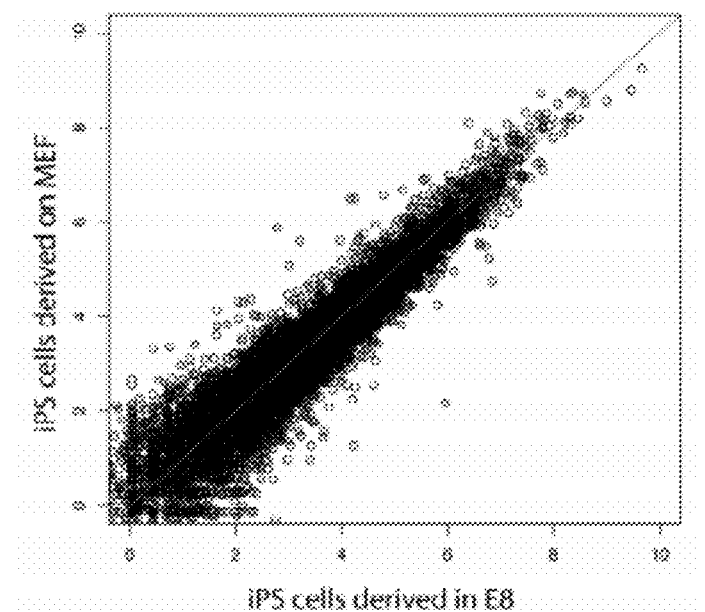

Figure 5
FIG. 5A
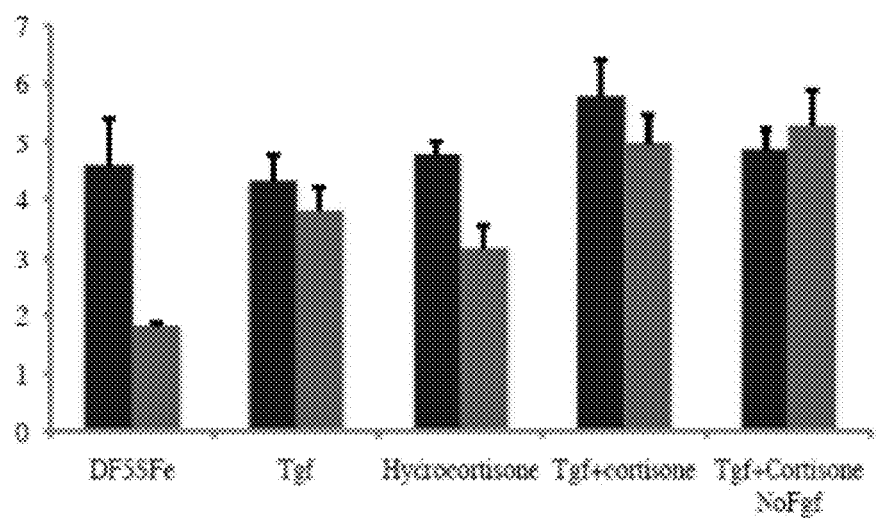
FIG. 5B
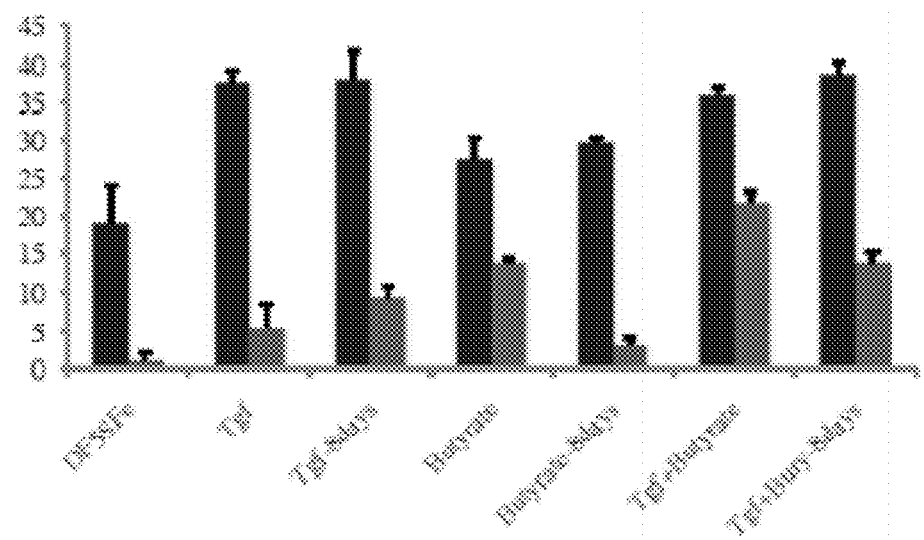

Figure 6
FIG. 6A
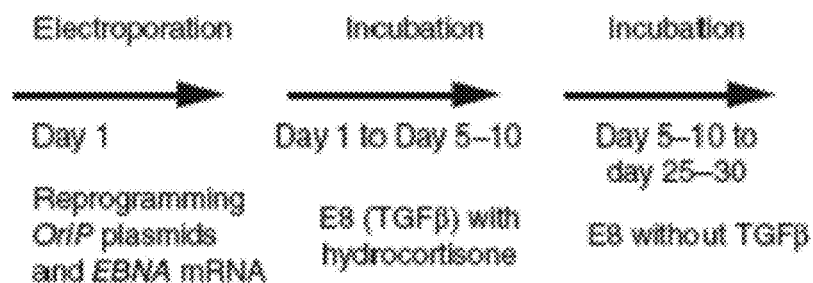
FIG. 6B
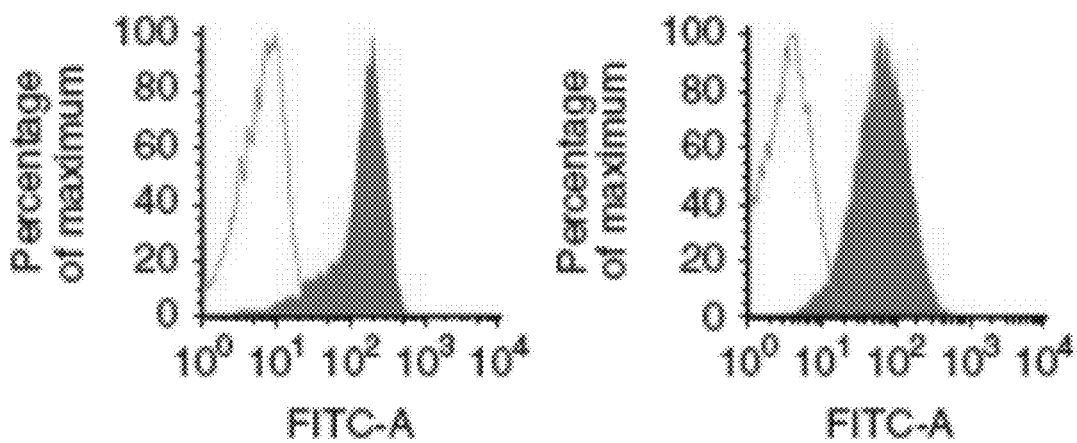

Figure 7
FIG. 7A
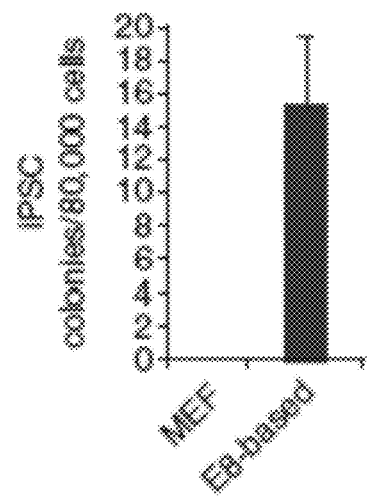
FIG. 7B
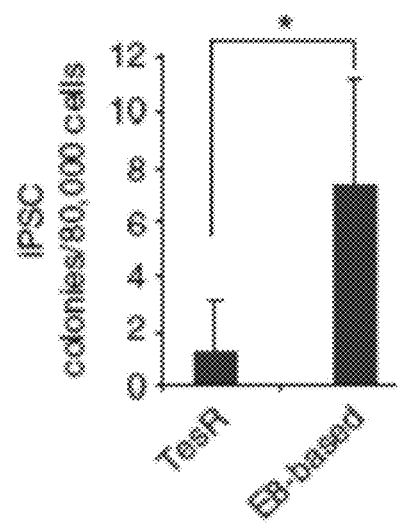

SEQUENCE LISTING

```
<160> NUMBER OF SEQ ID NOS: 11

<210> SEQ ID NO 1
<211> LENGTH: 1411
<212> TYPE: DNA
<213> ORGANISM: Homo sapiens

<400> SEQUENCE: 1
ccttcgcaag ccctcatttc accaggcccc cggcttgggg cgccttcctt ccccatggcg      60
ggacacctgg cttcggattt cgccttctcg cccccctccag gtggtggagg tgatgggcca    120 gggggggccgg agccgggctg ggttgatcct cggacctggc taagcttcca aggccctcct    180
ggagggccag gaatcgggcc gggggttggg ccaggctctg aggtgtgggg gattccccca    240
tgccccccgc cgtatgagtt ctgtgggggg atggcgtact gtgggcccca ggttggagtg    300
gggctagtgc cccaaggcgg cttggagacc tctcagcctg agggcgaagc aggagtcggg    360
gtggagagca actccgatgg ggcctccccg gagccctgca ccgtcacccc tggtgccgtg    420
aagctggaga aggagaagct ggagcaaaac ccggaggagt cccaggacat caaagctctg    480
cagaaagaac tcgagcaatt tgccaagctc ctgaagcaga agaggatcac cctgggatat    540
acacaggccg atgtgggggct caccctgggg gttctatttg ggaaggtatt cagccaaacg    600
accatctgcc gctttgaggc tctgcagctt agcttcaaga acatgtgtaa gctgcggccc    660
```

```
ttgctgcaga agtgggtgga ggaagctgac aacaatgaaa atcttcagga gatatgcaaa      720
gcagaaaccc tcgtgcaggc ccgaaagaga aagcgaacca gtatcgagaa ccgagtgaga      780
ggcaacctgg agaatttgtt cctgcagtgc ccgaaaccca cactgcagca gatcagccac      840
atcgcccagc agcttgggct cgagaaggat gtggtccgag tgtggttctg taaccggcgc      900
cagaagggca agcgatcaag cagcgactat gcacaacgag aggattttga ggctgctggg      960
tctcctttct caggggggacc agtgtccttt cctctggccc cagggcccca ttttggtacc     1020
ccaggctatg ggagccctca cttcactgca ctgtactcct cggtccctttt ccctgagggg     1080 gaagcctttc cccctgtctc cgtcaccact ctgggctctc ccatgcattc aaactgaggt     1140
gcctgccctt ctaggaatgg gggacagggg gaggggagga gctagggaaa gaaaacctgg     1200
agtttgtgcc agggttttg ggattaagtt cttcattcac taaggaagga attgggaaca      1260
caaagggtgg gggcagggga gtttggggca actggttgga gggaaggtga agttcaatga     1320
tgctcttgat tttaatccca catcatgtat cacttttttc ttaaataaag aagcctggga     1380
cacagtagat agacacactt aaaaaaaaaa a                                     1411

<210> SEQ ID NO 2
<211> LENGTH: 2518
<212> TYPE: DNA
<213> ORGANISM: Homo sapiens

<400> SEQUENCE: 2
ctattaactt gttcaaaaaa gtatcaggag ttgtcaaggc agagaagaga gtgtttgcaa       60
aagggggaaa gtagtttgct gccctcttaa gactaggact gagagaaaga agaggagaga     120
gaaagaaagg gagagaagtt tgagccccag gcttaagcct ttccaaaaaa taataataac     180
aatcatcggc ggcggcagga tcggccagag gaggagggaa gcgcttttttt tgatcctgat     240 tccagtttgc ctctctcttt ttttccccca aattattctt cgcctgattt tcctcgcgga     300
gccctgcgct cccgacaccc ccgcccgcct ccctcctcc tctccccccg ccgcgggcc      360 ccccaaagtc ccggccgggc cgagggtcgg cggccgccgg cgggccgggc ccgcgcacag     420
cgcccgcatg tacaacatga tggagacgga gctgaagccg ccgggcccgc agcaaacttc     480 gggggggcggc ggcggcaact ccaccgcggc ggcggccggc ggcaaccaga aaaacagccc     540
ggaccgcgtc aagcggccca tgaatgcctt catggtgtgg tcccgcgggc agcggcgcaa     600
gatgggccag gagaacccca agatgcacaa ctcggagatc agcaagcgcc tgggcgccga     660
gtggaaactt ttgtcggaga cggagaagcg gccgttcatc gacgaggcta gcggctgcg     720 agcgctgcac atgaaggagc acccggatta taaataccgg ccccggcgga aaaccaagac      780
gctcatgaag aaggataagt acacgctgcc cggcggctg ctggccccg gcggcaatag      840 catggcgagc ggggtcgggg tgggcgccgg cctgggcgcg ggcgtgaacc agcgcatgga     900
cagttacgcg cacatgaacg gctggagcaa cggcagctac agcatgatgc aggaccagct     960
gggctacccg cagcacccgg gcctcaatgc gcacggcgca gcgcagatgc agcccatgca     1020
ccgctacgac gtgagcgccc tgcagtacaa ctccatgacc agctcgcaga cctacatgaa     1080
cggctcgccc acctacagca tgtcctactc gcagcagggc acccctggca tggctcttgg     1140
ctccatgggt tcggtggtca gtccgaggc cagctccagc ccccctgtgg ttacctcttc     1200
ctcccactcc agggcgccct gcaggccgg ggacctccgg gacatgatca gcatgtatct     1260
ccccggcgcc gaggtgccgg aacccgccgc ccccagcaga cttcacatgt cccagcacta     1320
```

-continued

| | | |
|---|---|---|
| ccagagcggc cggtgcccg gcacggccat taacggcaca ctgcccctct cacacatgtg | 1380 | |
| agggccggac agcgaactgg aggggggaga aattttcaaa gaaaaacgag ggaaatggga | 1440 | |
| ggggtgcaaa agaggagagt aagaaacagc atggagaaaa cccggtacgc tcaaaaagaa | 1500 | |
| aaaggaaaaa aaaaaatccc atcacccaca gcaaatgaca gctgcaaaag agaacaccaa | 1560 | |
| tcccatccac actcacgcaa aaaccgcgat gccgacaaga aaactttat gagagagatc | 1620 | |
| ctggacttct ttttggggga ctattttgt acagagaaaa cctggggagg gtggggaggg | 1680 | |
| cggggggaatg gaccttgtat agatctggag gaaagaaagc tacgaaaaac ttttaaaag | 1740 | |
| ttctagtggt acgtaggag ctttgcagga agtttgcaaa agtctttacc aataatattt | 1800 | |
| agagctagtc tccaagcgac gaaaaaaatg ttttaatatt tgcaagcaac ttttgtacag | 1860 | |
| tatttatcga gataaacatg gcaatcaaaa tgtccattgt ttataagctg agaatttgcc | 1920 | |
| aatatttttc aaggagaggc ttcttgctga attttgattc tgcagctgaa atttaggaca | 1980 | |
| gttgcaaacg tgaaagaag aaaattattc aaatttggac attttaattg tttaaaaatt | 2040 | |
| gtacaaaagg aaaaaattag aataagtact ggcgaaccat ctctgtggtc ttgtttaaaa | 2100 | |
| agggcaaaag ttttagactg tactaaattt tataacttac tgttaaaagc aaaaatggcc | 2160 | |
| atgcaggttg acaccgttgg taatttataa tagcttttgt tcgatcccaa cttcccattt | 2220 | |
| tgttcagata aaaaaaacca tgaaattact gtgtttgaaa tattttctta tggtttgtaa | 2280 | |
| tatttctgta aatttattgt gatatttaa ggttttcccc cctttatttt ccgtagttgt | 2340 | |
| attttaaaag attcggctct gtattatttg aatcagtctg ccgagaatcc atgtatatat | 2400 | |
| ttgaactaat atcatcctta taacaggtac attttcaact taagtttta ctccattatg | 2460 | |
| cacagtttga gataaataaa ttttttgaaat atggacactg aaaaaaaaaa aaaaaaa | 2518 | |

<210> SEQ ID NO 3
<211> LENGTH: 2098
<212> TYPE: DNA
<213> ORGANISM: Homo sapiens

<400> SEQUENCE: 3

| | | |
|---|---|---|
| attataaatc tagagactcc aggattttaa cgttctgctg gactgagctg gttgcctcat | 60 | |
| gttattatgc aggcaactca cttttatccca atttcttgat acttttcctt ctggaggtcc | 120 | |
| tatttctcta acatcttcca gaaaagtctt aaagctgcct taaccttttt tccagtccac | 180 | |
| ctcttaaatt ttttcctcct cttcctctat actaacatga gtgtggatcc agcttgtccc | 240 | |
| caaagcttgc cttgctttga agcatccgac tgtaaagaat cttcacctat gcctgtgatt | 300 | |
| tgtgggcctg aagaaaacta ccatccttg caaatgtctt ctgctgagat gcctcacacg | 360 | |
| gagactgtct ctcctcttcc ttcctccatg gatctgctta ttcaggacag ccctgattct | 420 | |
| tccaccagtc ccaaaggcaa acaacccact tctgcagaga agagtgtcgc aaaaaaggaa | 480 | |
| gacaaggtcc cggtcaagaa acagaagacc agaactgtgt tctcttccac ccagctgtgt | 540 | |
| gtactcaatg atagatttca gagacagaaa tacctcagcc tccagcagat gcaagaactc | 600 | |
| tccaacatcc tgaacctcag ctacaaacag gtgaagacct ggttccagaa ccagagaatg | 660 | |
| aaatctaaga ggtggcagaa aaacaactgg ccgaagaata gcaatggtgt gacgcagaag | 720 | |
| gcctcagcac ctacctaccc cagcctttac tcttcctacc accagggatg cctggtgaac | 780 | |
| ccgactggga accttccaat gtggagcaac cagacctgga caattcaac ctggagcaac | 840 | |
| cagacccaga acatccagtc ctggagcaac cactcctgga cactcagac ctggtgcacc | 900 | |
| caatcctgga acaatcaggc ctggaacagt cccttctata actgtggaga ggaatctctg | 960 | |

```
cagtcctgca tgcagttcca gccaaattct cctgccagtg acttggaggc tgccttggaa    1020
gctgctgggg aaggccttaa tgtaatacag cagaccacta ggtattttag tactccacaa    1080
accatggatt tattcctaaa ctactccatg aacatgcaac ctgaagacgt gtgaagatga    1140
gtgaaactga tattactcaa tttcagtctg acactggct gaatccttcc tctcccctcc     1200
tcccatccct cataggattt ttcttgtttg gaaaccacgt gttctggttt ccatgatgcc    1260
catccagtca atctcatgga gggtggagta tggttggagc taatcagcg aggtttcttt     1320 tttttttttt ttcctattgg atcttcctgg agaaaatact ttttttttttt ttttttttga    1380 aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctccct    1620
aacagctggg atttacaggc gtgagccacc gcgccctgcc tagaaaagac attttaataa    1680
ccttggctgc cgtctctggc tatagataag tagatctaat actagtttgg atatctttag    1740
ggtttagaat ctaaccctcaa gaataagaaa tacaagtaca aattggtgat gaagatgtat   1800
tcgtattgtt tgggattggg aggctttgct tattttttaa aaactattga ggtaaagggt    1860
taagctgtaa catacttaat tgatttctta ccgttttttgg ctctgttttg ctatatcccc   1920
taatttgttg gttgtgctaa tctttgtaga aagaggtctc gtatttgctg catcgtaatg    1980
acatgagtac tgctttagtt ggtttaagtt caaatgaatg aaacaactat ttttcctta     2040 gttgatttta ccctgatttc accgagtgtt tcaatgagta aatatacagc ttaaacat     2098

<210> SEQ ID NO 4
<211> LENGTH: 4014
<212> TYPE: DNA
<213> ORGANISM: Homo sapiens

<400> SEQUENCE: 4
gtgcggggga agatgtagca gcttcttctc cgaaccaacc ctttgccttc ggacttctcc       60
ggggccagca gccgcccgac caggggcccg ggccacggg ctcagccgac gaccatgggc       120
tccgtgtcca accagcagtt tgcaggtggc tgcgccaagg cggcagaaga ggcgcccgag      180
gaggcgccgg aggacgcggc ccgggcggcg gacgagcctc agctgctgca cggtgcgggc      240
atctgtaagt ggttcaacgt gcgcatgggg ttcggcttcc tgtccatgac cgcccgcgcc      300
ggggtcgcgc tcgaccccc agtggatgtc tttgtgcacc agagtaagct gcacatggaa      360
gggttccgga gcttgaagga gggtgaggca gtggagttca cctttaagaa gtcagccaag     420
ggtctggaat ccatccgtgt caccggacct ggtgagtat tctgtattgg gagtgagagg      480
cggccaaaag gaaagagcat gcagaagcgc agatcaaaag gagacaggtg ctacaactgt      540
ggaggtctag atcatcatgc caaggaatgc aagctgccac cccagcccaa gaagtgccac      600
ttctgccaga gcatcagcca tatggtagcc tcatgtccgc tgaaggccca gcagggccct      660
agtgcacagg gaaagccaac ctactttcga gaggaagaag aagaaatcca cagccctacc     720
ctgctcccgg aggcacagaa ttgagccaca atgggtgggg ctattctttt gctatcagg      780 aagttttgag gagcaggcag agtggagaaa gtgggaatag ggtgcattgg ggctagttgg     840
cactgccatg tatctcaggc ttgggttcac accatcaccc tttcttccct ctaggtgggg    900
ggaaagggtg agtcaaagga actccaacca tgctctgtcc aaatgcaagt gagggttctg    960
```

```
ggggcaacca ggagggggga atcaccctac aacctgcata ctttgagtct ccatccccag   1020
aatttccagc ttttgaaagt ggcctggata gggaagttgt tttccttttta aagaaggata   1080 tataataatt cccatgccag agtgaaatga ttaagtataa gaccagattc atggagccaa   1140
gccactacat tctgtggaag gagatctctc aggagtaagc attgtttttt tttcacatct   1200
tgtatcctca tacccacttt tgggataggg tgctggcagc tgtcccaagc aatgggtaat   1260
gatgatggca aaaagggtgt ttgggggaac agctgcagac ctgctgctct atgctcaccc   1320 ccgcccatt ctgggccaat gtgattttat ttatttgctc ccttggatac tgcaccttgg    1380
gtcccacttt ctccaggatg ccaactgcac tagctgtgtg cgaatgacgt atcttgtgca   1440
ttttaacttt ttttccttaa tataaatatt ctggttttgt attttttgtat attttaatct  1500 aaggccctca tttcctgcac tgtgttctca ggtacatgag caatctcagg atagccagc    1560 agcagctcca ggtctgcgca gcaggaatta cttttttgttg tttttgccac cgtggagagc  1620
aactatttgg agtgcacagc ctattgaact acctcatttt tgccaataag agctggcttt   1680
tctgccatag tgtcctcttg aaaccccctc tgccttgaaa atgttttatg ggagactagg   1740
ttttaactgg gtggcccat gacttgattg ccttctactg gaagattggg aattagtcta    1800
aacaggaaat ggtggtacac agaggctagg agaggctggg cccggtgaaa aggccagaga   1860
gcaagccaag attaggtgag ggttgtctaa tcctatggca caggacgtgc tttacatctc   1920
cagatctgtt cttcaccaga ttaggttagg cctaccatgt gccacagggt gtgtgtgtgt   1980
ttgtaaaact agagttgcta aggataagtt taaagaccaa taccctgta cttaatcctg    2040 tgctgtcgag ggatggatat atgaagtaag gtgagatcct taacctttca aaattttcgg   2100
gttccaggga gacacacaag cgagggtttt gtggtgcctg gagcctgtgt cctgccctgc   2160
tacagtagtg attaatagtg tcatggtagc taaaggagaa aaaggggggtt tcgtttacac  2220 gctgtgagat caccgcaaac ctaccttact gtgttgaaac gggacaaatg caatagaacg   2280
cattgggtgg tgtgtgtctg atcctgggtt cttgtctccc ctaaatgctg cccccaagt    2340 tactgtatt gtctgggctt tgtaggactt cactacgttg attgctaggt ggcctagttt    2400
gtgtaaatat aatgtattgg tcttctccg tgttctttgg gggttttgtt tacaaacttc    2460
tttttgtatt gagagaaaaa tagccaaagc atctttgaca gaaggttctg caccaggcaa   2520
aaagatctga acattagtt tggggggccc tcttcttaaa gtggggatct tgaaccatcc    2580
tttcttttgt attcccttc ccctattacc tattagacca gatcttctgt cctaaaaact    2640
tgtcttctac cctgccctct tttctgttca ccccaaaag aaaacttaca cacccacaca    2700
catacacatt tcatgcttgg agtgtctcca caactcttaa atgatgtatg caaaaatact   2760
gaagctagga aaaccctcca tcccttgttc ccaacctcct aagtcaagac cattaccatt   2820 tcttttctttc tttttttttt tttttaaaa tggagtctca ctgtgtcacc caggctggag   2880
tgcagtggca tgatcggctc actgcagcct ctgcctcttg ggttcaagtg attctcctgc   2940
ctcagcctcc tgagtagctg ggattcagg caccgccac actcagctaa ttttttgtatt   3000 tttagtagag acggggtttc accatgttgt ccaggctggt ctggaactcc tgacctcagg   3060
tgatctgccc accttggctt cccaaagtgc tgggattaca ggcatgagcc accatgctgg   3120
gccaaccatt tcttggtgta ttcatgccaa acacttaaga cactgctgta gcccaggcgc   3180
ggtggctcac acctgtaatc ccagcacttt ggaaggctga ggcgggcgga tcacaaggtc   3240
acgagttcaa aactatcctg gccaacacag tgaaaccccg tctctactaa aatacaaaaa   3300
aattagccgg gtgtggtggt gcatgccttt agtcctagct attcaggagg ctgaggcagg   3360
```

| | | | | |
|---|---|---|---|---|
| ggaatcgctt | gaacccgaga | ggcagaggtt | gcagtgagct | gagatcgcac | cactgcactc | 3420 |
| cagcctggtt | acagagcaag | actctgtctc | aaacaaaaca | aaacaaaaca | aaacacact | 3480 |
| actgtatttt | ggatggatca | aacctcctta | attttaattt | ctaatcctaa | agtaaagaga | 3540 |
| tgcaattggg | ggccttccat | gtagaaagtg | gggtcaggag | gccaagaaag | gaatatgaa | 3600 |
| tgtatatcca | agtcactcag | gaactttat | gcaggtgcta | gaaactttat | gtcaaagtgg | 3660 |
| ccacaagatt | gtttaatagg | agacgaacga | atgtaactcc | atgttactg | ctaaaaacca | 3720 |
| aagctttgtg | taaaatcttg | aatttatggg | gcgggagggt | aggaaagcct | gtacctgtct | 3780 |
| gtttttttcc | tgatccttt | ccctcattcc | tgaactgcag | gagactgagc | cccttgggc | 3840 |
| tttggtgacc | ccatcactgg | ggtgtgttta | tttgatggtt | gattttgctg | tactgggtac | 3900 |
| ttcctttccc | atttctaat | cattttttaa | cacaagctga | ctcttccctt | ccttctcct | 3960 |
| ttccctggga | aaatacaatg | aataaataaa | gacttattgg | tacgcaaact | gtca | 4014 |

<210> SEQ ID NO 5
<211> LENGTH: 2377
<212> TYPE: DNA
<213> ORGANISM: Homo sapiens

<400> SEQUENCE: 5

| | | | | |
|---|---|---|---|---|
| accccccgagc | tgtgctgctc | gcggccgcca | ccgccgggcc | ccggccgtcc | ctggctcccc | 60 |
| tcctgcctcg | agaagggcag | ggcttctcag | aggcttggcg | ggaaaaagaa | cggagggagg | 120 |
| gatcgcgctg | agtataaaag | ccggttttcg | gggctttatc | taactcgctg | tagtaattcc | 180 |
| agcgagaggc | agagggagcg | agcgggcggc | cggctagggt | ggaagagccg | ggcgagcaga | 240 |
| gctgcgctgc | gggcgtcctg | gaagggaga | tccggagcga | ataggggct | tcgcctctgg | 300 |
| cccagccctc | ccgctgatcc | cccagccagc | ggtccgcaac | ccttgccgca | tccacgaaac | 360 |
| tttgcccata | gcagcgggcg | ggcactttgc | actggaactt | acaacacccg | agcaaggacg | 420 |
| cgactctccc | gacgcgggga | ggctattctg | cccatttggg | gacacttccc | cgccgctgcc | 480 |
| aggacccgct | tctctgaaag | gctctccttg | cagctgctta | gacgctggat | ttttttcggg | 540 |
| tagtggaaaa | ccagcagcct | cccgcgacga | tgccctcaa | cgttagcttc | accaacagga | 600 |
| actatgacct | cgactacgac | tcggtgcagc | cgtattcta | ctgcgacgag | gaggagaact | 660 |
| tctaccagca | gcagcagcag | agcgagctgc | agccccggc | gcccagcgag | gatatctgga | 720 |
| agaaattcga | gctgctgccc | accccgcccc | tgtccctag | ccgccgctcc | gggctctgct | 780 |
| cgccctccta | cgttgcggtc | acacccttct | cccttcgggg | agacaacgac | ggcggtggcg | 840 |
| ggagcttctc | cacggccgac | cagctggaga | tggtgaccga | gctgctggga | ggagacatgg | 900 |
| tgaaccagag | tttcatctgc | gacccggacg | acgagacctc | catcaaaaac | atcatcatcc | 960 |
| aggactgtat | gtggagcggc | ttctcggccg | ccgccaagct | cgtctcagag | aagctggcct | 1020 |
| cctaccagge | tgcgcgcaaa | gacagcggca | gcccgaaccc | cgcccgcggc | cacagcgtct | 1080 |
| gctccacctc | cagcttgtac | ctgcaggatc | tgagcgccgc | cgcctcagag | tgcatcgacc | 1140 |
| cctcggtggt | cttcccctac | cctctcaacg | acagcagctc | gcccaagtcc | tgcgcctcgc | 1200 |
| aagactccag | cgccttctct | ccgtcctcgg | attctctgct | ctcctcgacg | gagtcctccc | 1260 |
| cgcagggcag | ccccgagccc | ctggtgctcc | atgaggagac | accgccacc | accagcagcg | 1320 |
| actctgagga | ggaacaagaa | gatgaggaag | aaatcgatgt | tgtttctgtg | aaaagaggc | 1380 |
| aggctcctgg | caaaaggtca | gagtctggat | caccttctgc | tggaggccac | agcaaacctc | 1440 |

| | |
|---|---|
| ctcacagccc actggtcctc aagaggtgcc acgtctccac acatcagcac aactacgcag | 1500 |
| cgcctccctc cactcggaag gactatcctg ctgccaagag ggtcaagttg acagtgtca | 1560 |
| gagtcctgag acagatcagc aacaaccgaa aatgcaccag ccccaggtcc tcggacaccg | 1620 |
| aggagaatgt caagaggcga acacacaacg tcttggagcg ccagaggagg aacgagctaa | 1680 |
| aacggagctt ttttgccctg cgtgaccaga tcccggagtt ggaaaacaat gaaaaggccc | 1740 |
| ccaaggtagt tatccttaaa aaagccacag catacatcct gtccgtccaa gcagaggagc | 1800 |
| aaaagctcat ttctgaagag gacttgttgc ggaaacgacg agaacagttg aaacacaaac | 1860 |
| ttgaacagct acggaactct tgtgcgtaag gaaaagtaag gaaaacgatt ccttctaaca | 1920 |
| gaaatgtcct gagcaatcac ctatgaactt gtttcaaatg catgatcaaa tgcaacctca | 1980 |
| caaccttggc tgagtcttga gactgaaaga tttagccata atgtaaactg cctcaaattg | 2040 |
| gactttgggc ataaaagaac ttttttatgc ttaccatctt ttttttttct ttaacagatt | 2100 |
| tgtatttaag aattgttttt aaaaaatttt aagatttaca caatgtttct ctgtaaatat | 2160 |
| tgccattaaa tgtaaataac tttaataaaa cgtttatagc agttacacag aatttcaatc | 2220 |
| ctagtatata gtacctagta ttataggtac tataaaccct aattttttt atttaagtac | 2280 |
| attttgcttt ttaaagttga ttttttttcta ttgttttag aaaaaataaa ataactggca | 2340 |
| aatatatcat tgagccaaaa aaaaaaaaaa aaaaaa | 2377 |

```
<210> SEQ ID NO 6
<211> LENGTH: 2949
<212> TYPE: DNA
<213> ORGANISM: Homo sapiens

<400> SEQUENCE: 6
```

| | |
|---|---|
| agtttcccga ccagagagaa cgaacgtgtc tgcgggcgcg cggggagcag aggcggtggc | 60 |
| gggcggcggc ggcaccggga gccgccgagt gaccctcccc cgcccctctg gccccccacc | 120 |
| ctcccacccg cccgtggccc gcgcccatgg ccgcgcgcgc tccacacaac tcaccggagt | 180 |
| ccgcgccttg cgccgccgac cagttcgcag ctccgcgcca cggcagccag tctcacctgg | 240 |
| cggcaccgcc cgcccaccgc cccggccaca gcccctgcgc ccacggcagc actcgaggcg | 300 |
| accgcgacag tggtggggga cgctgctgag tggaagagag cgcagcccgg ccaccggacc | 360 |
| tacttactcg ccttgctgat tgtctatttt tgcgtttaca acttttctaa gaacttttgt | 420 |
| atacaaagga acttttttaaa aaagacgctt ccaagttata tttaatccaa agaagaagga | 480 |
| tctcggccaa tttggggttt tgggtttttgg cttcgtttct tctcttcgtt gactttgggg | 540 |
| ttcaggtgcc ccagctgctt cgggctgccg aggaccttct gggcccccac attaatgagg | 600 |
| cagccacctg gcgagtctga catggctgtc agcgacgcgc tgctcccatc tttctccacg | 660 |
| ttcgcgtctg gcccggcggg aagggagaag acactgcgtc aagcaggtgc cccgaataac | 720 |
| cgctggcggg aggagctctc ccacatgaag cgacttcccc cagtgcttcc cggccgcccc | 780 |
| tatgacctgg cggcggcgac cgtggccaca gacctggaga gcggcggagc cggtgcggct | 840 |
| tgcggcggta gcaacctggc gcccctacct cggagagaga ccgaggagtt caacgatctc | 900 |
| ctggacctgg actttattct ctccaattcg ctgacccatc ctccggagtc agtgccgcc | 960 |
| accgtgtcct cgtcagcgtc agcctcctct tcgtcgtcgc cgtcgagcag cggccctgcc | 1020 |
| agcgcgccct ccacctgcag cttcacctat ccgatccggg ccgggaacga ccgggcgtg | 1080 |
| gcgccgggcg gcacgggcgg aggcctcctc tatggcaggg agtccgctcc ccctccgacg | 1140 |
| gctcccttca cctggcgga catcaacgac gtgagcccct cgggcggctt cgtggccgag | 1200 |

```
ctcctgcggc cagaattgga cccggtgtac attccgccgc agcagccgca gccgccaggt    1260
ggcgggctga tgggcaagtt cgtgctgaag gcgtcgctga gcgcccctgg cagcgagtac    1320
ggcagcccgt cggtcatcag cgtcagcaaa ggcagccctg acggcagcca cccggtggtg    1380
gtggcgccct acaacggcgg gccgccgcgc acgtgcccca agatcaagca ggaggcggtc    1440
tcttcgtgca cccacttggg cgctggaccc cctctcagca atggccaccg gccggctgca    1500
cacgacttcc ccctggggcg gcagctcccc agcaggacta ccccgaccct gggtcttgag    1560
gaagtgctga gcagcaggga ctgtcaccct gccctgccgc ttcctcccgg cttccatccc    1620
cacccggggc ccaattaccc atccttcctg cccgatcaga tgcagccgca gtcccgccg    1680 ctccattacc aagagctcat gccacccggt tcctgcatgc cagaggagcc caagccaaag    1740
aggggaagac gatcgtggcc ccggaaaagg accgccaccc acacttgtga ttacgcgggc    1800
tgcggcaaaa cctacacaaa gagttcccat ctcaaggcac acctgcgaac ccacacaggt    1860
gagaaacctt accactgtga ctgggacggc tgtggatgga aattcgcccg ctcagatgaa    1920
ctgaccaggc actaccgtaa acacacgggg caccgcccgt tccagtgcca aaaatgcgac    1980
cgagcatttt ccaggtcgga ccacctcgcc ttacacatga agaggcattt ttaaatccca    2040
gacagtggat atgacccaca ctgccagaag agaattcagt atttttttact tttcacactg    2100 tcttcccgat gagggaagga gcccagccag aaagcactac aatcatggtc aagttcccaa    2160
ctgagtcatc ttgtgagtgg ataatcagga aaatgagga tccaaaaga caaaaatcaa    2220 agaacagatg gggtctgtga ctggatcttc tatcattcca attctaaatc cgacttgaat    2280
attcctggac ttacaaaatg ccaaggtggt gactggaagt tgtggatatc agggtataaa    2340
ttatatccgt gagttggggg agggaagacc agaattccct tgaattgtgt attgatgcaa    2400
tataagcata aagatcacc ttgtattctc tttaccttct aaaagccatt attatgatgt    2460
tagaagaaga ggaagaaatt caggtacaga aacatgttt aaatagccta atgatggtg    2520 cttggtgagt cttggttcta aaggtaccaa acaaggaagc caaagttttc aaactgctgc    2580
atactttgac aaggaaaatc tatatttgtc ttccgatcaa catttatgac ctaagtcagg    2640
taatatacct ggtttacttc tttagcattt ttatgcagac agtctgttat gcactgtggt    2700
ttcagatgtg caataatttg tacaatggtt tattcccaag tatgccttaa gcagaacaaa    2760 tgtgttttttc tatatagttc cttgccttaa taaatatgta atataaattt aagcaaacgt    2820
ctattttgta tatttgtaaa ctacaaagta aaatgaacat tttgtggagt ttgtattttg    2880
catactcaag gtgagaatta agttttaaat aaacctataa tattttatct gaaaaaaaa    2940 aaaaaaaa                                                             2949
```

<210> SEQ ID NO 7
<211> LENGTH: 2949
<212> TYPE: DNA
<213> ORGANISM: Simian virus 40

<400> SEQUENCE: 7

```
agtttcccga ccagagagaa cgaacgtgtc tgcgggcgcg cggggagcag aggcggtggc      60
gggcggcggc ggcaccggga gccgccgagt gaccctcccc cgcccctctg gccccccacc     120
ctcccacccg cccgtggccc gcgcccatgg ccgcgcgcgc tccacacaac tcaccggagt     180
ccgcgccttg cgccgccgac cagttcgcag ctccgcgcca cggcagccag tctcacctgg     240
cggcaccgcc cgcccaccgc cccggccaca gccctgcgc ccacggcagc actcgaggcg     300
```

```
accgcgacag tggtggggga cgctgctgag tggaagagag cgcagcccgg ccaccggacc    360
tacttactcg ccttgctgat tgtctatttt tgcgtttaca acttttctaa gaactttttgt   420
atacaaagga acttttttaaa aaagacgctt ccaagttata tttaatccaa agaagaagga   480
tctcggccaa tttggggttt tgggttttgg cttcgtttct tctcttcgtt gactttgggg    540
ttcaggtgcc ccagctgctt cgggctgccg aggaccttct gggcccccac attaatgagg    600
cagccacctg gcgagtctga catggctgtc agcgacgcgc tgctcccatc tttctccacg    660
ttcgcgtctg gcccggcggg aagggagaag acactgcgtc aagcaggtgc cccgaataac    720
cgctggcggg aggagctctc ccacatgaag cgacttcccc cagtgcttcc ggccgcccc    780
tatgacctgg cggcggcgac cgtggccaca gacctggaga gcggcggagc cggtgcggct    840
tgcggcggta gcaacctggc gcccctacct cggagagaga ccgaggagtt caacgatctc    900
ctggacctgg actttattct ctccaattcg ctgacccatc ctccggagtc agtggccgcc    960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagcccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccggtggtg   1380
gtggcgcccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccgggc ccaattaccc atccttcctg cccgatcaga tgcagccgca agtcccgccg    1680
ctccattacc aagagctcat gccacccggt tcctgcatgc cagaggagcc caagccaaag   1740
agggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga agaggcattt ttaaatccca   2040
gacagtggat atgacccaca ctgccagaag agaattcagt attttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaagggggt gactggaagt tgtggatatc agggtataaa   2340
ttatatccgt gagttggggg agggaagacc agaattccct tgaattgtgt attgatgcaa   2400
tataagcata aaagatcacc ttgtattctc tttaccttct aaaagccatt attatgatgt   2460
tagaagaaga ggaagaaatt caggtacaga aaacatgttt aaatagccta aatgatggtg   2520
cttggtgagt cttggttcta aaggtaccaa acaaggaagc caaagttttc aaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
```

-continued

```
ttcagatgtg caataatttg tacaatggtt tattcccaag tatgccttaa gcagaacaaa    2760
tgtgttttc tatatagttc cttgccttaa taaatatgta atataaattt aagcaaacgt    2820
ctattttgta tatttgtaaa ctacaaagta aaatgaacat tttgtggagt ttgtattttg    2880
catactcaag gtgagaatta agttttaaat aaacctataa tattttatct gaaaaaaaaa    2940
aaaaaaaaa                                                             2949
```

<210> SEQ ID NO 8
<211> LENGTH: 4018
<212> TYPE: DNA
<213> ORGANISM: Homo sapiens

<400> SEQUENCE: 8

```
caggcagcgc tgcgtcctgc tgcgcacgtg ggaagccctg ccccggcca ccccgcgat      60
gccgcgcgct ccccgctgcc gagccgtgcg ctccctgctg cgcagccact accgcgaggt   120
gctgccgctg gccacgttcg tgcggcgcct ggggccccag ggctggcggc tggtgcagcg   180
cggggacccg gcggcttcc gcgcgctggt ggcccagtgc ctggtgtgcg tgccctggga   240
cgcacggccg cccccccgccg cccctcctt ccgccaggtg tcctgcctga aggagctggt   300
ggcccgagtg ctgcagaggc tgtgcgagcg cggcgcgaag aacgtgctgg ccttcggctt   360
cgcgctgctg gacggggccc gcggggggccc cccgaggcc ttcaccacca gcgtgcgcag   420
ctacctgccc aacacggtga ccgacgcact gcggggagc gggcgtggg ggctgctgct   480
gcgccgcgtg ggcgacgacg tgctggttca cctgctggca cgctgcgcgc tctttgtgct   540
ggtggctccc agctgcgcct accaggtgtg cgggccgccg ctgtaccagc tcggcgctgc   600
cactcaggcc cggccccccgc cacacgctag tggacccgga aggcgtctgg gatgcgaacg   660
ggcctggaac catagcgtca gggaggccgg ggtcccctg ggcctgccag ccccgggtgc    720
gaggaggcgc gggggcagtg ccagccgaag tctgccgttg cccaagaggc ccaggcgtgg   780
cgctgccct gagccggagc ggacgcccgt tgggcagggg tcctgggccc acccgggcag    840
gacgcgtgga ccgagtgacc gtggtttctg tgtggtgtca cctgccagac ccgccgaaga   900
agccacctct ttggagggtg cgctctctgg cacgcgccac tcccacccat ccgtgggccg   960
ccagcaccac gcgggccccc catccacatc gcggccacca cgtccctggg acacgccttg  1020
tcccccggtg tacgccgaga ccaagcactt cctctactcc tcaggcgaca aggagcagct  1080
gcggccctcc ttcctactca gctctctgag gcccagcctg actggcgctc ggaggctcgt  1140
ggagaccatc tttctgggtt ccaggccctg gatgccaggg actccccgca ggttgccccg  1200
cctgccccag cgctactggc aaatgcggcc cctgtttctg gagctgcttg ggaaccacgc  1260
gcagtgcccc tacggggtgc tcctcaagac gcactgcccg ctgcgagctg cggtcacccc  1320
agcagccggt gtctgtgccc gggagaagcc ccagggctct gtggcggccc ccgaggagga  1380
ggacacagac cccgtcgcc tggtgcagct gctccgccag cacagcagcc cctggcaggt  1440
gtacggcttc gtgcgggcct gcctgcgccg gctggtgccc ccaggcctct ggggctccag  1500
gcacaacgaa cgccgcttcc tcaggaacac caagaagttc atctccctgg ggaagcatgc  1560
caagctctcg ctgcaggagc tgacgtgaa gatgagcgtg cgggactgcg cttggctgcg  1620
caggagccca ggggttggct gtgttccggc cgcagagcac cgtctgcgtg aggagatcct  1680
ggccaagttc ctgcactggc tgatgagtgt gtacgtcgtc gagctgctca ggtctttctt  1740
ttatgtcacg gagaccacgt ttcaaaagaa caggctcttt ttctaccgga agagtgtctg  1800
```

-continued

```
gagcaagttg caaagcattg aatcagaca gcacttgaag agggtgcagc tgcgggagct    1860
gtcggaagca gaggtcaggc agcatcggga agccaggccc gccctgctga cgtccagact    1920
ccgcttcatc cccaagcctg acgggctgcg gccgattgtg aacatggact acgtcgtggg    1980
agccagaacg ttccgcagag aaagagggc cgagcgtctc acctcgaggg tgaaggcact    2040
gttcagcgtg ctcaactacg agcgggcgcg gcgccccggc ctcctgggcg cctctgtgct    2100
gggcctggac gatatccaca gggcctggcc caccttcgtg ctgcgtgtgc gggcccagga    2160
cccgccgcct gagctgtact tgtcaaggt ggatgtgacg ggcgcgtacg acaccatccc    2220
ccaggacagg ctcacggagg tcatcgccag catcatcaaa cccagaaca cgtactgcgt    2280
gcgtcggtat gccgtggtcc agaaggccgc ccatgggcac gtccgcaagg ccttcaagag    2340
ccacgtctct accttgacag acctccagcc gtacatgcga cagttcgtgg ctcacctgca    2400
ggagaccagc ccgctgaggg atgccgtcgt catcgagcag agctcctccc tgaatgaggc    2460
cagcagtggc ctcttcgacg tcttcctacg cttcatgtgc caccacgccg tgcgcatcag    2520
gggcaagtcc tacgtccagt gccaggggat cccgcagggc tccatcctct ccacgctgct    2580
ctgcagcctg tgctacggcg acatggaaa caagctgttt gcggggattc ggcgggacgg    2640
gctgctcctg cgtttggtgg atgatttctt gttggtgaca cctcacctca cccacgcgaa    2700
aaccttcctc aggaccctgg tccgaggtgt ccctgagtat ggctgcgtgg tgaacttgcg    2760
gaagacagtg gtgaacttcc ctgtagaaga cgaggccctg ggtggcacgg cttttgttca    2820
gatgccggcc cacggcctat tccctggtgt cggcctgctg ctggatacccc ggaccctgga    2880
ggtgcagagc gactactcca gctatgcccg gacctccatc agagccagtc tcaccttcaa    2940
ccgcggcttc aaggctggga ggaacatgcg tcgcaaactc tttggggtct gcggctgaa    3000
gtgtcacagc ctgtttctgg atttgcaggt gaacagcctc cagacggtgt gcaccaacat    3060
ctacaagatc ctcctgctgc aggcgtacag gtttcacgca tgtgtgctgc agctcccatt    3120
tcatcagcaa gtttggaaga ccccacatt tttcctgcgc gtcatctctg acacggcctc    3180
cctctgctac tccatcctga aagccaagaa cgcagggatg tcgctggggg ccaagggcgc    3240
cgccggccct ctgccctccg aggccgtgca gtggctgtgc caccaagcat tcctgctcaa    3300
gctgactcga caccgtgtca cctacgtgcc actcctgggg tcactcagga cagcccagac    3360
gcagctgagt cggaagctcc cggggacgac gctgactgcc ctggaggccg cagccaaccc    3420
ggcactgccc tcagacttca agaccatcct ggactgatgg ccacccgccc acagccaggc    3480
cgagagcaga caccagcagc cctgtcacgc cgggctctac gtcccaggga gggaggggcg    3540
gcccacaccc aggcccgcac cgctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccag ctttccctca ccaggagccc ggcttccact ccccacatag gaatagtcca    3780
tccccagatt cgccattgtt caccccctcgc cctgccctcc tttgccttcc accccccacca    3840
tccaggtgga gaccctgaga aggaccctgg gagctctggg aatttggagt gaccaaaggt    3900
gtgccctgta cacaggcgag gaccctgcac ctggatgggg gtccctgtgg gtcaaattgg    3960
ggggaggtgc tgtgggagta aaatactgaa tatatgagtt tttcagtttt gaaaaaaa    4018
```

<210> SEQ ID NO 9
<211> LENGTH: 585
<212> TYPE: DNA
<213> ORGANISM: Encephalomyocarditis virus

<400> SEQUENCE: 9

```
gccctctcc ctccccccc cctaacgtta ctggccgaag ccgcttggaa taaggccggt      60
gtgcgtttgt ctatatgtta ttttccacca tattgccgtc ttttggcaat gtgagggccc    120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
tctgcggcca aaagccacgt gtataagata cacctgcaaa ggcggcacaa ccccagtgcc    360
acgttgtgag ttggatagtt gtggaaagag tcaaatggct ctcctcaagc gtattcaaca    420
aggggctgaa ggatgcccag aaggtacccc attgtatggg atctgatctg gggcctcggt    480
gcacatgctt tacatgtgtt tagtcgaggt taaaaaaacg tctaggcccc ccgaaccacg    540
gggacgtggt tttcctttga aaaacacgat gataatatgg ccaca                    585
```

<210> SEQ ID NO 10
<211> LENGTH: 589
<212> TYPE: DNA
<213> ORGANISM: Human cytomegalovirus

<400> SEQUENCE: 10

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatc                589
```

<210> SEQ ID NO 11
<211> LENGTH: 1192
<212> TYPE: DNA
<213> ORGANISM: Homo sapiens

<400> SEQUENCE: 11

```
ctagcttcgt gaggctccgg tgcccgtcag tgggcagagc gcacatcgcc cacagtcccc     60
gagaagttgg gggagggggt cggcaattga accggtgcct agagaaggtg gcgcggggta    120
aactgggaaa gtgatgtcgt gtactggctc cgccttttc ccgagggtgg gggagaaccg    180
tatataagtg cagtagtcgc cgtgaacgtt ctttttcgca acgggtttgc cgccagaaca    240
caggtaagtg ccgtgtgtgg ttcccgcggg cctggcctct ttacgggtta tggcccttgc    300
gtgccttgaa ttacttccac ctggctccag tacgtgattc ttgatcccga gctggagcca    360
ggggcgggcc ttgcgcttta ggagcccctt cgcctcgtgc ttgagttgag gcctggcctg    420
ggcgctgggg ccgccgcgtg cgaatctggt ggcaccttcg cgcctgtctc gctgctttcg    480
ataagtctct agccatttaa aattttgat gacctgctgc gacgcttttt ttctggcaag    540
atagtcttgt aaatgcgggc caggatctgc acactggtat ttcggttttt gggcccgcgg    600
```

-continued

```
ccggcgacgg ggcccgtgcg tcccagcgca catgttcggc gaggcggggc ctgcgagcgc    660
ggccaccgag aatcggacgg gggtagtctc aagctggccg gcctgctctg gtgcctggcc    720
tcgcgccgcc gtgtatcgcc ccgccctggg cggcaaggct ggcccggtcg gcaccagttg    780
cgtgagcgga aagatggccg cttcccggcc ctgctccagg gggctcaaaa tggaggacgc    840
ggcgctcggg agagcgggcg ggtgagtcac ccacacaaag gaaaagggcc tttccgtcct    900
cagccgtcgc ttcatgtgac tccacggagt accgggcgcc gtccaggcac ctcgattagt    960
tctggagctt ttggagtacg tcgtctttag gttgggggga ggggtttat gcgatggagt    1020 ttccccacac tgagtgggtg gagactgaag ttaggccagc ttggcacttg atgtaattct    1080
cgttggaatt tgcccttttt gagtttggat cttggttcat tctcaagcct cagacagtgg    1140
ttcaaagttt ttttcttcca tttcaggtgt cgtgaacacg tggtcgcggc ca            1192
```

SIMPLIFIED BASIC MEDIA FOR HUMAN PLURIPOTENT CELL CULTURE

STATEMENT REGARDING FEDERALLY SPONSORED RESEARCH OR DEVELOPMENT

This invention was made with government support under ES017166 awarded by the National Institutes of Health. The government has certain rights in the invention.

CROSS-REFERENCE TO RELATED APPLICATIONS

This application claims the benefit of U.S. Provisional Patent Application Ser. No. 61/371,128 filed on Aug. 5, 2010.

BACKGROUND

Pluripotent cells, such as embryonic stem (ES) cells and induced pluripotent stem (iPS) cells, have the potential to differentiate into cells of all three primary germ layers (Thomson, et al., Science 282, 1145-1147 (1998)). The remarkable developmental potential of pluripotent cells has proven useful for basic research and clinical application. Many basic methods for human pluripotent cell culture, such as growth media, plate coating, and other conditions, have been developed and refined (Ludwig et al., Nat. Biotechnol 24, 185-187 (2006); Ludwig et al., Nat. Methods 3, 637-646 (2006)). For example, while human ES cells were initially cultured in fetal bovine serum (FBS)-containing media on murine embryonic fibroblast (MEF) feeder cells, fully defined media as well as defined protein matrices are now available (Ludwig et al., Nat. Biotechnol 24, 185-187 (2006)).

Over the past ten years, pluripotent cell culture methods have evolved considerably. Several growth media were developed that provide basic nutrients and growth factors for survival and expansion of pluripotent cells and directly determine how cells grow and differentiate. TeSR™ was one of the first defined media that supports pluripotent cell maintenance in an undifferentiated state in the absence of feeder cells or conditioned medium through multiple culture passages (Ludwig et al., Nat. Methods 3, 637-646 (2006); U.S. Pat. No. 7,449,334, each of which is incorporated herein by reference as if set forth in its entirety). TeSR™ contains 18 components in addition to the basal medium DMEM/F12 that itself has 52 components (Table 1).

The variety of different growth media available for pluripotent cell culture contributes to inconsistencies in research findings. The media that are presently used for pluripotent cell derivation and growth, including fully defined media, contain components that can influence pluripotent cells in various ways. Prior to the invention described herein, it was not known how each media component, alone or in combination with other components, affects various pluripotent cell functions such as viability, pluripotency, or differentiation in cell culture.

For example, albumin, the most abundant protein component present in most media, is a lipid carrier and, as such, can affect differentiation or maintenance of pluripotency via its associated lipids. The qualities of albumin and of its associated lipids determine whether it can be used for human pluripotent cell culture. However, albumin quality varies greatly depending on its source, even when produced from a recombinant genetic material, contributing to variations between experiments conducted under otherwise equivalent conditions. Also, while cloned human serum albumin is available, it is seldom used for routine experimentation due to its comparatively high cost.

Efforts to eliminate albumin from the medium have proved unsuccessful. Omission of albumin, or any other growth factor present in TeSR, led to a dramatic decline in human ESC culture performance, such as decreased cell viability, proliferation, and pluripotency (Ludwig et al., Nat. Biotechnol 24, 185-187 (2006)).

To fully exploit the potential of pluripotent cells for drug discovery, testing, and transplantation therapy, derivation and growth of these cells under fully-defined and, ideally, xeno-free, conditions is desirable. There is, thus an unmet need in the art for media free of components that introduce inconsistencies to maintain control over pluripotent cell culture conditions. Specifically, there is a need in the art for pluripotent cell culture media containing only those components that support pluripotent cell functions important for a specific culture objective.

BRIEF SUMMARY

The invention relates generally to media, compositions, and methods for deriving and culturing pluripotent cells, and more particularly, to fully-defined media for pluripotent cells.

In a first aspect, the present invention is summarized as albumin-free media that support viability, growth, and pluripotency of pluripotent cells.

In some embodiments of the first aspect, the medium contains selenium.

In some embodiments of the first aspect, the medium contains NODAL.

In some embodiments of the first aspect, the medium contains transferrin.

In some embodiments of the first aspect, the medium contains transforming growth factor beta (TGF-β).

In some embodiments of the first aspect, the medium contains only water, salts, amino acids, vitamins, a carbon source, insulin, and a fibroblast growth factor (FGF), each in amounts sufficient to support pluripotent stem cell viability.

In some embodiments of the first aspect, the medium contains only water, salts, amino acids, vitamins, a carbon source, insulin, an FGF, selenium, transferrin, and one of TGF-β and NODAL, each in an amount sufficient to support pluripotent stem cell proliferation.

In some embodiments of the first aspect, the medium supports survival after passaging, freezing, proliferation, pluripotency, derivation, and cloning of pluripotent cells.

In some embodiments of the first aspect, the medium is xeno-free.

In a second aspect, the present invention is summarized as a method for culturing pluripotent stem cells in a defined medium. In some embodiments of the second aspect, the medium used to culture pluripotent cells contains only water, salts, amino acids, vitamins, a carbon source, insulin, and an FGF, each in amounts sufficient to support pluripotent cell viability. In some embodiments of the second aspect, the medium used to culture pluripotent cells contains only water, salts, amino acids, vitamins, a carbon source, insulin, an FGF, selenium, transferrin, and one of TGF-β and NODAL, each in an amount sufficient to support pluripotent stem cell proliferation. In some embodiments of the second aspect, the medium contains defined factors that support extended growth, pluripotency, cloning, freezing, or derivation of pluripotent cells. In some embodiments of the second aspect, the medium used to culture pluripotent cells is xeno-free.

In a third aspect, the present invention is directed to an in vitro cell culture composition of pluripotent cells in a medium that is substantially free of β-mercaptoethanol and albumin. In some embodiments of the third aspect, the culture composition is free of fibroblast feeder cells, conditioned medium, and xeno-contamination.

In a fourth aspect, the present invention is summarized as a method for deriving iPS cells from an adult individual under completely defined conditions. The method includes the steps of culturing a somatic cell from an adult individual in a medium containing water, salts, amino acids, vitamins, a carbon source, insulin, and an FGF, all in sufficient amount to maintain viability, and reprogramming the cell in defined conditions such as to derive iPS cells.

In some embodiments of the fourth aspect, the medium contains TGF-β during parts or all of the reprogramming process.

In some embodiments of the fourth aspect, the medium contains butyrate.

In some embodiments of the fourth aspect, the medium contains hydrocortisone.

In some embodiments of the fourth aspect, the medium is xeno-free.

In a fifth aspect, the present invention is summarized as a method for cloning a pluripotent stem cell in an albumin-free medium. The method includes the step of plating pluripotent stem cells at cloning density in an albumin-free medium that supports pluripotent stem cell cloning.

In some embodiments of the fifth aspect, the medium contains a ROCK inhibitor.

In some embodiments of the fifth aspect, the medium contains blebbistatin.

In some embodiments of the fifth aspect, the medium contains only water, salts, amino acids, vitamins, a carbon source, insulin, an FGF, selenium, transferrin, and one of TGF-β and NODAL, each in an amount sufficient to support pluripotent stem cell cloning.

In a sixth aspect, the present invention is summarized as a method of cryopreserving pluripotent stem cells in an albumin-free medium. The method includes the step of freezing pluripotent stem cells in an albumin-free medium.

In some embodiments of the sixth aspect, the medium contains only water, salts, amino acids, vitamins, a carbon source, insulin, an FGF, selenium, transferrin, one of TGF-β and NODAL, and dimethyl sulfoxide (DMSO).

In a seventh aspect, the invention is summarized as an iPS cell derived under albumin-free conditions. iPS cells derived in the absence of albumin are free of endogenous albumin contaminations.

The methods and compositions described herein are useful in a variety of applications for deriving, culturing, and using pluripotent cells. It is an object of the present invention to define short term and long term culture conditions for pluripotent cells limited to factors that support the intended culture objective.

It is another object of the present invention to provide culture conditions for pluripotent cells that maximize percentage of cultured cells in an undifferentiated state.

It is another object of the present invention to provide media that can serve as the platform necessary to examine how various conditions affect pluripotent cells and to compare experiments previously reported in different media backgrounds.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1A-E illustrate media elements for human ES cell survival and self-renewal in culture. FIG. 1A illustrates 24 hour survival indices for individualized cells plated in the various media. Media abbreviations are as listed in Table 1. The presence of insulin and fibroblast growth factor (IF), bovine serum albumin (BSA), beta-mecaptoethanol (BME) is indicated by "+" and absence is indicated by "−." FIG. 1B illustrates 24 hour or 96 hour survival indices for individualized cells plated in the various media. The addition of insulin and fibroblast growth factor (FGF) is indicated by "+" and removal is indicated by "−." FIG. 1C illustrates 24 hour or 129 hour survival indices for individualized cells cultured in TeSR™ medium with Vitamin C (TeSR), TeSR™ medium without Vitamin C (TeSR™-LAA), or DF5 medium. FIG. 1D illustrates cell proliferation after each of three passages in DF5, DF5 with added Selenium (DF5+Selenium), DF12, or DF12 from which Selenium had been removed (DF12-Selenium). FIG. 1E illustrates a comparative analysis of twelve different base media.

FIG. 2A-F illustrate optimization of human ES cell and iPS cell culture conditions with DF5S. FIG. 2A shows survival indices for individualized cells that were seeded at low density (~1,500 cells/cm$^2$) in either DF5S (bottom) or TeSR™ (top) and cultured at different $O_2$ and $CO_2$ concentrations (O15C5: 15% $O_2$ and 5% $CO_2$; O15C10: 15% $O_2$ and 10% $CO_2$; O5C10: 5% $O_2$ and 10% $CO_2$). Cell survival was examined at 24 hours and 124 hours. FIG. 2B shows the cloning efficiency of H1 cells cultured in various media in the presence (+HA100) or absence of the small molecule HA100 (CM100: conditioned media with 100 ng/ml FGF). FIG. 2C shows the cloning efficiency of H1 cells and iPS cells derived from foreskin fibroblasts in various media. FIG. 2D shows the cloning efficiency of iPS cells derived from foreskin fibroblasts in various media. DF5S trFe indicates DF5S media to which holotransferrin was added. FIG. 2E illustrates the cloning efficiency of H1 cells cultured in various media in the presence of HA100 (10 μM, 24 hours), blebbistatin (10 μM, 4 hours), or Y27632 (10 μM, 24 hours), compared to cloning efficiency in the absence of these factors (control). Asterisks indicate $p<0.05$. FIG. 2F illustrates cloning efficiency of H1 cells in conditioned medium (CM), CM with ROCK inhibitor (HA100), TeSR with ROCK inhibitor, and E8 with ROCK inhibitor in normoxic (dark gray bars) or hypoxic (light gray bars) conditions. Error bars indicate the standard error of the mean; asterisks indicate $p<0.05$.

FIG. 3 A-B illustrate pluripotent cell growth and gene expression in DMEM/F12 supplemented with insulin, transferrin, selenium, L-ascorbic acid, FGF2, and TGF-β or NODAL (referred to herein as "E8 (TGF-β)" and "E8 (NODAL)," respectively). FIG. 3A illustrates fold expansion of H1 ES cells (top) and iPS cells (bottom) maintained in TeSR™ (dark gray lines) or E8 (TGF-β) (light gray lines). FIG. 3B illustrates global gene expression of H1 ES cells grown in E8 (TGF-β) and H1 ES cells grown in TeSR™. RNA of H1 cells maintained in either TeSR or E8 (TGF-β) medium for 3 passages was analyzed by RNA-seq with Illumina Genome Analyzer GAIIX (global gene expression correlation R=0.954 (Spearman Correlation)).

FIG. 4A-F illustrate iPS cell derivation under defined conditions. FIG. 4A shows proliferation of foreskin fibroblasts in DF5SFe-based media to which various fibroblast growth factors (FGF) were added, compared to proliferation in FBS-containing media. FIG. 4B shows fibroblast growth in various media supplemented with hydrocortisone. FIG. 4C shows expression of the pluripotency markers OCT4 (left) and SSEA4 (right). FIG. 4D illustrates expression of selected genes by foreskin fibroblasts, hES cells, iPS cells derived on feeder cells (iPS Cells (Feeder)), and iPS cells derived in E8 medium (iPS Cells (E8)). All cells were maintained in E8 (TGF-β) medium prior to RNA analysis, except for fibroblasts, which were maintained in E8 with hydrocortisone. FIG. 4E illustrates global gene expression of human ES and iPS cells derived in E8 (TGF-β) media (R=0.955). FIG. 4F global gene expression of iPS cells derived on MEF and iPS cells derived in E8 (TGF-β) media.

FIG. 5A-C illustrate media improvement for iPS cell derivation. FIG. 5A shows proliferation of foreskin (dark grey bars) and PRPF8-2 adult fibroblasts (light grey bars) in DF5SFe media supplemented with TGF-β, hydrocortisone, TGF-β and hydrocortisone, or TGF-β and hydrocortisone without FGF. FIG. 5B illustrates the effect of TGF-β and butyrate on reprogramming of foreskin fibroblasts. Four to five weeks after initial reprogramming transfection, colony numbers for transformed cells and true iPS cells were scored and the ratio of iPS colonies to non-iPS cell colonies was calculated.

FIG. 6A-B illustrate derivation of iPS cells from adult fibroblasts under fully-defined conditions without secondary passage. FIG. 6A illustrates an example of a reprogramming protocol. FIG. 6B illustrates expression of the pluripotency markers OCT4 and SSEA4, as determined by flow cytometric analysis of iPSC lines maintained in DMEM/F12 supplemented with insulin, transferrin, selenium, L-ascorbic acid, FGF2, and TGF-β or NODAL ("E8") for 20 passages. Shaded peak: staining with antibodies specific to OCT4 (left) and SSEA4 (right); unshaded peak: mouse IgG control antibody.

FIG. 7A-C illustrate reprogramming efficiency of human fibroblasts in various media. FIG. 7A illustrates the number of iPS cell colonies per 80,000 fibroblasts subjected to reprogramming with mouse fibroblast feeder cells (MEF) or in E8-based medium. To improve efficiency, 100 μM sodium butyrate was added to both conditions. FIG. 7B illustrates the number of iPS cell colonies per 80,000 fibroblasts subjected to reprogramming in TeSR™ or in E8-based medium. FIG. 7C illustrates the effects of TGF-β and butyrate exposure time on reprogramming efficiency of foreskin fibroblasts under fully-defined conditions. Fibroblasts were reprogrammed in DMEM/F12 supplemented with insulin, transferrin, selenium, L-ascorbic acid, and FGF2 (E8 without TGF-β) or in E8, in the presence or absence of 100 μM butyrate. Reprogramming efficiency for all conditions was analyzed after 30 days after reprogramming. Asterisks indicate p<0.05.

Figures 1, 1E:
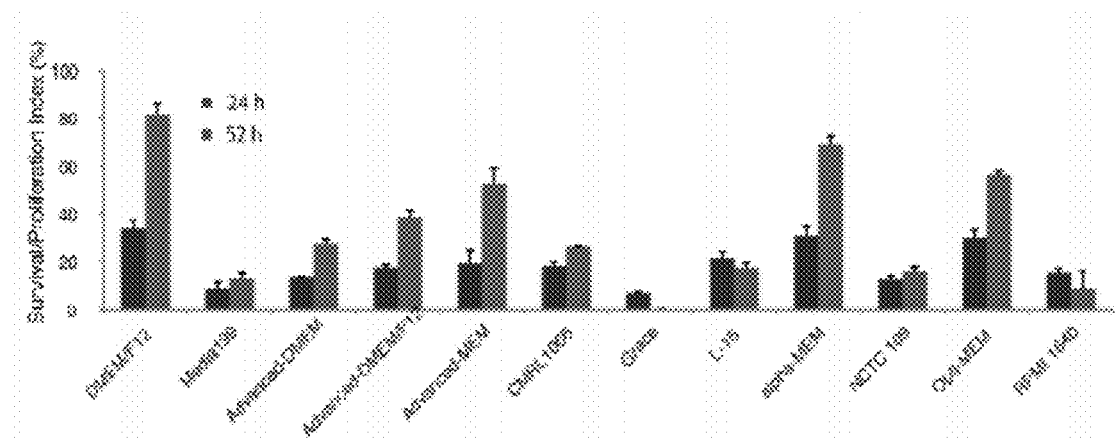

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

The present invention relates to the inventors' observation that certain media components once thought to be essential to culturing pluripotent cells can be omitted from pluripotent cell culture media formulated to achieve certain culture objectives.

As used herein, the term "pluripotent cell" means a cell capable of differentiating into cells of all three germ layers. Examples of pluripotent cells include embryonic stem cells and induced pluripotent stem (iPS) cells. As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g. multipotent or somatic) cells.

The invention relates to new media free of factors not essential for a particular culture objective. Examples of culture objectives include, but are not limited to, cell survival, passaging, proliferation, pluripotency, cloning, and iPS cell derivation. Specifically, the invention relates to albumin-free media.

As a point of clarification, "passaging" and "cloning" are distinct methods. "Passaging" describes the process of dividing cells that have been cultivated in a culture vessel up to a certain density into aggregates, which are then placed into new culture vessels. These aggregates can contain any number of cells, typically between 100 to 1,000 cells, which readily initiate growth in culture. In contrast, "cloning" refers to initiating clonal colonies by growing human ES cell colonies from single individual ES cells. As used herein, "cloning efficiency" means the number of individualized cells that form new cell colonies divided by the number of individualized cells plated in culture. Cloning efficiency varies considerably depending on culture conditions. For example, the cloning efficiency of human ES cells under defined and xeno-free conditions on MATRIGEL® is very low (i.e., less than about 0.1%), while cloning efficiency of these cells cultured with fibroblast-conditioned medium, while still low (i.e., less than about 2%), is high enough to initiate clonal ES cell colonies.

Certain media components presently used can be damaging to the cultured cells or induce differentiation. For example, β-mercaptoethanol can damage and even kill cultured pluripotent cells. Serum media additives, such as bovine serum albumin (BSA) or fetal calf serum (FCS), can induce differentiation of cultured pluripotent cells. Also, commercially available serum components can differ significantly in their composition, even when supplied from the same source, introducing unpredictable culture variability. The media described herein are substantially free of damaging, differentiating, and undefined factors present in most conventional pluripotent cell culture media. The disclosed media have been successfully used for various culture objectives, such as supporting short term pluripotent cells viability, e.g., 24 hrs, short term proliferation, e.g., 4-5 days, maintaining pluripotent cells for extended culture periods, e.g., more than 25 passages in 3 months, and to derive iPS cells from both fetal and adult fibroblasts with lentiviral and episomal vectors.

New minimal media specifically tailored for certain cell culture objectives were developed. Various media components, such as salts, vitamins, glucose sources, minerals, and amino acids were tested, alone or in combination, to determine their individual effect on viability, proliferation, or pluripotency. A new survival assay was developed and used to determine which components are essential for pluripotent cell survival after dissociation. New media were tested for their ability to support proliferation and sustain pluripotency. These media were also used in cloning assays to determine how each medium affects single cells and their cloning efficiency. A complete list of ingredients for each new medium described herein is set forth in Table 1 (light and dark shaded fields indicate presence of a component in the medium, checkered fields indicate interchangeable components, clear fields indicate absence of a component in the medium).

appreciates the advantageous efficiency of using a basal media as starting material to prepare the disclosed new media. The term "basal medium" as used herein means a medium that supports growth of certain single-celled organisms and cells that do not require special media additives. Typical basal medium components are known in the art and include salts, amino acids, vitamins, and a carbon source (e.g., glucose). Other components that do not change the basic characteristic of the medium but are otherwise desirable can also be included, such as the pH indicator phenol red. For example, Dulbecco's Modified Eagle Medium: Nutrient Mixture F-12 (DMEM/F12) is a basal medium commonly used to make

TABLE 1

Media compositions.

| Components | GF | NM | DF5 | DF5S | DF5SFe | DF12 | TeSR | DF5S + TGF-β | DF5S + NODAL | DF5S + HCort | E8 |
|---|---|---|---|---|---|---|---|---|---|---|---|
| DMEM/F12 |  | ▨ | ■ | ▨ | ■ | ▨ | ■ | ▨ | ▨ | ▨ |  |
| NaHCO3 |  | ▨ |  | ▨ |  | ▨ | ■ | ▨ | ■ | ▨ |  |
| L-Ascorbic Acid |  | ▨ |  | ▨ | ■ | ▨ | ■ | ▨ | ■ | ▨ | ■ |
| Selenium |  | ▨ |  | ▨ | ■ | ▨ | ■ | ▨ | ■ | ▨ | ■ |
| Transferrin |  | ▨ |  |  | ■ |  | ■ |  |  |  |  |
| Glutathione |  | ▨ |  |  |  |  | ■ |  |  |  |  |
| L-Glutamine |  | ▨ |  |  |  |  | ■ |  |  |  |  |
| Defined lipids |  | ▨ |  |  |  |  | ■ |  |  |  |  |
| Thiamine |  | ▨ |  |  |  |  | ■ |  |  |  |  |
| Trace elements B |  | ▨ |  |  |  |  | ■ |  |  |  |  |
| Trace elements C |  | ▨ |  |  |  |  | ■ |  |  |  |  |
| BME |  | ▨ |  |  |  |  | ■ |  |  |  |  |
| BSA |  | ▨ |  |  |  |  | ■ |  |  |  |  |
| Insulin | ■ |  |  | ▨ | ■ | ▨ | ■ | ▨ | ■ | ▨ | ■ |
| FGF2 | ■ |  |  | ▨ | ■ | ▨ | ■ | ▨ | ■ | ▨ | ■ |
| TGF-β |  |  |  |  |  |  | ■ | ■ |  |  | ▨ |
| Pipecolic acid |  |  |  |  |  |  |  |  |  |  |  |
| LiCl | ■ |  |  |  |  |  |  |  |  |  |  |
| GABA | ■ |  |  |  |  |  |  |  |  |  |  |
| H2O |  |  |  |  |  |  |  |  |  |  |  |
| Nodal |  |  |  |  |  |  |  |  | ■ |  | ▨ |
| Hydrocortisone |  |  |  |  |  |  |  |  |  | ▨ |  |

The various media described herein can be prepared from the basic ingredients. Alternatively, one of skill in the art appreciates suitable growth media for mammalian cell culture. A complete list of ingredients of DMEM/F12 is set forth in Table 2.

TABLE 2

DMEM: F-12 Medium Formulation (ATCC Catalog No. 30-2006).

| Inorganic Salts (g/liter) | Amino Acids (g/liter) | Vitamins (g/liter) | Other (g/liter) |
|---|---|---|---|
| CaCl2 (anhydrous) 0.11665 | L-Alanine 0.00445 | D-Biotin 0.00000365 | D-Glucose 3.15100 |
| CuSO4 (anhydrous) 0.0000008 | L-Arginine•HCl 0.14750 | Choline Chloride 0.00898 | HEPES 3.57480 |
| Fe(NO3)3•9H2O 0.00005 | L-Asparagine•H2O 0.00750 | Folic Acid 0.00265 | Hypoxanthine 0.00239 |
| FeSO4•7H2O 0.000417 | L-Aspartic Acid 0.00665 | myo-Inositol 0.01261 | Linoleic Acid 0.000044 |
| MgSO4 (anhydrous) 0.08495 | L-Cystine•HCl•H2O 0.01756 | Niacinamide 0.00202 | Phenol Red, Sodium Salt 0.00810 |
| KCl 0.3118 | L-Cystine•2HCl 0.03129 | D-Pantothenic Acid 0.00224 | Putrescine•2HCl 0.00008 |
| NaHCO3 1.20000 | L-Glutamic Acid 0.00735 | Pyridoxine•HCl 0.00203 | Pyruvic Acid•Na 0.05500 |
| NaCl 7.00000 | L-Glutamine 0.36510 | Riboflavin 0.00022 | DL-Thioctic Acid 0.000105 |
| Na2HPO4 (anhydrous) 0.07100 | Glycine 0.01875 | Thiamine•HCl 0.00217 | Thymidine 0.000365 |
| NaH2PO4•H2O 0.06250 | L-Histidine•HCl•H2O 0.03148 | Vitamin B-12 0.00068 |  |
| ZnSO4•7H2O 0.000432 | L-Isoleucine 0.05437 |  |  |
|  | L-Leucine 0.05895 |  |  |
|  | L-Lysine•HCl 0.09135 |  |  |
|  | L-Methionine 0.01724 |  |  |
|  | L-Phenylalanine 0.03548 |  |  |
|  | L-Proline 0.01725 |  |  |

TABLE 2-continued

DMEM: F-12 Medium Formulation (ATCC Catalog No. 30-2006).

| Inorganic Salts (g/liter) | Amino Acids (g/liter) | Vitamins (g/liter) | Other (g/liter) |
|---|---|---|---|
| | L-Serine 0.02625 | | |
| | L-Threonine 0.05355 | | |
| | L-Tryptophan 0.00902 | | |
| | L-Tyrosine•2Na•2H2O 0.05582 | | |
| | L-Valine 0.05285 | | |

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, "about" means within 5% of a stated concentration range or within 5% of a stated time frame.

As used herein, "essentially serum-free" means that a medium does not contain serum or serum replacement, or that it contains essentially no serum or serum replacement. For example, an essentially serum-free medium can contain less than about 10%, 9%, 8%, 7%, 6%, 5%, 4%, 3%, 2% or 1% serum, wherein the culturing capacity of the medium is still observed.

The term "defined culture medium" or "defined medium," as used herein, means that the identity and quantity of each medium ingredient is known.

As used herein, "a medium consisting essentially of" means a medium that contains the specified ingredients and, optionally, other ingredients that do not materially affect its basic characteristics.

As used herein, "effective amount" means an amount of an agent sufficient to evoke a specified cellular effect according to the present invention.

As used herein, "viability" means the state of being viable. Pluripotent cells that are viable attach to the cell plate surface and do not stain with the dye propidium iodide absent membrane disruption. Short term viability relates to the first 24 hours after plating the cells in culture. Typically, the cells do not proliferate in that time.

As used herein, "short term growth" means cell proliferation for 4-5 days in culture.

As used herein, "extended growth" means growth for at least five passages. Typically, media are tested for their ability to support pluripotent cell growth for more than twenty passages (approximately 2-3 months).

As used herein, "long-term culture" means more than 15 passages (approximately two months in culture).

As used herein, "pluripotency" means a cell's ability to differentiate into cells of all three germ layers.

As used herein, "cloning" means a process of initiating a cell culture from a starting culture, ideally, from a single pluripotent cell or at least from very few cells. Culture conditions that permit clonal culture of undifferentiated pluripotent cells may be the most demanding conditions of all of those required in normal pluripotent cell culture and proliferation.

As used herein, "iPS cell derivation" means reprogramming a cell that is not pluripotent to become pluripotent.

As used herein, "xeno-free" means cell culture conditions free of any cell or cell product of species other than that of the cultured cell.

As used herein, "normoxic condition" means conditions with about 20% oxygen.

As used herein, "hypoxic condition" means conditions with less than about 20% oxygen, e.g., about 5% oxygen.

The invention will be more fully understood upon consideration of the following non-limiting Examples.

EXAMPLES

Example 1

Pluripotent Cell Survival Assay

Five-hundred micro liter of various test media was loaded into each well of 12-well plates prior to the addition of cells. Adherent pluripotent cells were dissociated with TrypLE (Invitrogen) for 5 minutes or until fully detached from the culture plates. TrypLE was neutralized by adding an equal volume of media to the culture. The cells were counted, washed, and resuspended in fresh media at a concentration of 300,000 to 1,000,000 cells/ml. Approximately 100 µl of this cell solution was added into each well of the 12-well plates and the cells were incubated at 37° C. with 5% $O_2$ and 10% $CO_2$. Cells were again dissociated at various time points using 0.4 ml TrypLE, which was subsequently neutralized with equal volumes of 10% FBS in DMEM. The cells were counted by flow cytometry. 5000 count bright beads were added to each sample as internal control (approximately 200 beads were counted for each sample). All experiments were performed in triplicates.

Example 2

Growth Factors for Survival and Short Term Growth

TeSR medium contains six growth factors, in addition to those present in the basal medium, fibroblast growth factor (FGF), transforming growth factor beta (TGF-β), γ-aminobutyric acid (GABA), pipecolic acid, lithium chloride (LiCl), and insulin (Table 1). A basic nutrient medium (NM) was created containing all TeSR™ components with the exception of these six growth factors. About $2 \times 10^5$ H1 ES cells were dissociated and plated on Matrigel. The survival index was determined after 24 h. NM alone could not support cell survival after dissociation. The addition of insulin to NM resulted in cell survival similar to that observed with TeSR™, but did not support cell growth (FIG. 1A). The addition of both insulin (20 ug/ml) and FGF2 (100 ng/ml) supported cell survival and additionally led to cell growth in 96 h that was comparable to that observed using TeSR™ medium (FIG. 1B). Thus, NM supplemented with FGF and Insulin supports human ES cell culture. Twelve different basal nutrient media supplemented as described above were able to support cell survival and growth (FIG. 1E).

Example 3

L-Ascorbic Acid Supports Short-Term Proliferation

NM contains 11 nutritional components, i.e., DMEM/F12, trace elements B, trace elements C, L-ascorbic acid, thiamine, selenium, L-glutamine, BSA, BME, sodium bicarbonate (NaHCO$_3$), and transferrin (Table 1). DMEM/F12 serves as basal medium and NaHCO$_3$ is used to modify the pH. To determine which other nutritional components were essential when insulin and FGF were present, each factor was added individually to DMEM/F12, NaHCO$_3$, insulin, and FGF. None of the nutritional factors were essential for survival after passaging, but L-ascorbic acid (64 mg/L) was necessary for cell proliferation after passaging (FIG. 1C). L-ascorbic acid, known as Vitamin C, is a major antioxidant and cofactor of several enzymes. Hydroxyproline could partially substitute for L-ascorbic acid. Human ES cells plated in DMEM/F12, NaHCO$_3$, L-ascorbic acid, insulin, and FGF (Defined Factors 5, "DF5," Table 1) maintained similar morphology as human ES cells plated into TeSR.

Example 4

Media Components for Extended Passage

DF5 supported cell growth for only one passage. After the second passage, cells attached poorly and eventually died (FIG. 1C). Cells could be passaged in NM+Insulin+FGF (data not shown) and DF12 (FIG. 1D, Table 1), suggesting that one or more factor present in NM+Insulin+FGF and DF12 is important for extended passage. Each nutritional factor present in NM was added individually to DF5 to determine its ability to support cell expansion after multiple passages. Addition of selenium alone was sufficient to support cell proliferation through multiple passages (FIG. 1D, DF5+ Selenium, "DF5S," Table 1).

DF5S was used to expand H1 cells. Cells grown in DF5S were more prone to differentiate than cells grown in TeSR™. However, H1 cells could be grown for several weeks (more than 15 passages), during which the cells maintained human ES cell morphology and high levels of OCT4 expression (FIG. 1E, FIG. 1F). H1 cells grown in DF5S to which either NODAL (100 ng/ml) or TGF-β (2 ng/ml) was added expressed significantly higher levels of NANOG mRNA, compared to H1 cells cultured in DF5S. DF5S+NODAL also supported pluripotency of the two tested human iPS cell lines, as determined by high expression of the pluripotency marker OCT4. All cells (hES cells and iPS cells) grown in DF5S with either NODAL or TGF-β maintained a normal karyotype after long-term passage.

Example 5

Hypoxia Improves Cell Growth and Cloning

H1 cells grew faster in the DF5S medium compared to cells grown in TeSR™ (FIGS. 1C and 2A). To optimize pluripotent cell growth conditions, cells were grown in DF5S with varying osmolarity, pH, oxygen level, and CO$_2$ level. To increase assay sensitivity only 5,000 cells were seeded in each well and analyzed for survival (24 h) and proliferation (124 h). The greatest improvements were noted when O$_2$ and CO$_2$ levels were varied. Ordinary culture conditions use oxygen at ~15% and CO$_2$ at 5% (O15C5). Higher CO$_2$ often led to slightly higher survival after 24 hours. Lower oxygen levels increased cell growth in both DF5S and TeSR™. Oxygen at 15% with CO$_2$ at 10% (O15C10), and oxygen at 5% with CO$_2$ at 10% (O5C10) increased cell survival (FIG. 2A). Cells failed to thrive at higher O$_2$ levels (O15C5 and O15C10), while they proliferated at lower oxygen levels (O5C10) (FIG. 2A). Cells in DF5S grew faster than those grown in TeSR™, and grew fastest at 5% O$_2$ and 10% CO$_2$ (FIG. 2A). Further decreases in oxygen level to 2% reduced cell growth compared to 5% O$_2$.

To determine cloning efficiency at various oxygen and CO$_2$ concentrations, 500 cells were seeded into each well. Even at low oxygen, cloning efficiency was too low (<2%) to determine effects of various conditions on cloning. HA100, a ROCK inhibitor known to increase cloning efficiency, was used to increase cloning efficiency for testing oxygen and CO$_2$ concentrations. Conditioned medium (CM), known to be the best medium for cloning, was used as control. The addition of HA100 significantly improved cloning efficiency in CM at both O5C10 and O15C5 and cloning efficiency was higher at the O5C10 than O15C5 (FIG. 2B). Cloning efficiency of cells in DF5S was comparable to that of cells in CM under both conditions (FIG. 2B).

Because of the positive impact of hypoxia on cell survival, some of the subsequent examples employ hypoxic conditions when cells were maintained at low density. However, when cells were not cultured at low cell density, experiments were conducted under both normoxic and hypoxic conditions (FIG. 2B).

Example 6

Improved iPS Cell Cloning Efficiency

To determine how DF5S affects cloning efficiency, two iPS cell lines were grown in DF5S and plated at cloning density (approximately 500 cells per 12-well plate well) in the presence of HA100. The cloning efficiency of iPS cells grown in DF5S was lower than that of iPS cells grown in either TeSR™ or CM (FIG. 2C), suggesting that a factor that enhances cloning efficiency is present in TeSR™ medium, but absent from DF5S. To identify such factor, individual TeSR™ components were added individually to DF5S and tested for effect on cloning efficiency. The addition of holo-transferrin to DF5S (DF5SFe) resulted in cloning efficiency comparable to that using TeSR™ (FIG. 2D). Transferrin also lead to noticeable improvement of cloning efficiency of H1 cells in DF5S medium.

The ROCK inhibitors HA100 and Y27632, and blebbistatin in DMEM/F12 supplemented with insulin, trasferrin, selenium, L-ascorbic acid, FGFs, and TGF-β (or NODAL; "E8"), increased cloning efficiency of H1 cells (FIG. 2E), which was further increased by the addition of transferrin and by culture under hypoxic conditions (FIG. 2F)). The cells maintained a normal karyotype after more than 25 passages.

Example 7

NODAL and TGF-β Support Long-Term Maintenance of H1 and iPS Cell Pluripotency in Albumin-Free Media As described in Example 3, human pluripotent cells, such as H1, H9, and iPS cells, could be grown and passaged over 15 times in DF5S but were prone to differentiate, such that extra care is needed to sustain pluripotency in DF5S. Because pluripotency could be maintained more easily in TeSR™, growth factors present in TeSR™ were added individually to DF5SFe used to grow H1 cells that were previously cultured in DF5S without differentiating to identify factors supporting long-term pluripotency. Cells were passaged approximately one day after reaching confluency, facilitating cell differentiation, and Oct4 expression, assessed by flow cytometry, was used as indicator of pluripotency.

Human pluripotent cells grown in DF5SFe elongated and lined up along each other, resembling a "spindle" shape just prior to differentiation. This phenotype is often observed at the onset of neural differentiation that is usually suppressed by the TGF-β/BMP pathway. Thus, recombinant proteins of the TGF-β pathway were tested for their ability to support long-term pluripotency. DF5SFe supplemented with NODAL ("E8 (NODAL)") used at TeSR™ concentration sustained high Oct4 expression. DF5SFe supplemented with TGF-β ("E8 (TGF-β)") used at TeSR™ concentration (0.6 ng/ml) supported low levels of Oct4 expression but was able to maintain high Oct4 expression when used at higher concentration (1 ng/ml).

Human ES cell lines, such as H1 and H9 have a culture history that includes exposure to various complex culture components, such as FBS, feeder cells, and knockout serum replacer. Exposure to these components could conceivably create dependency on these components and, consequently, alter cellular response to simplified media. Culture history might play a lesser role for iPS cells, derived from reprogrammed somatic cells, as derivation conditions are less complex. Therefore, different factors were tested with two original lentiviral iPS cell lines (Yu, et al., Science 318:1917 (2007)) grown in DF5SFe. Cells were transferred from MEF plates directly into DF5SFe medium for one passage and then passaged into various growth factor conditions. The addition of either TGF-β (2 ng/ml) or NODAL (100 ng/ml) to DF5SFe ("E8 (TGF-β)" and "E8 (NODAL)," respectively) supported long-term pluripotency of iPS cells. Pluripotency surface markers SSEA4, SSEA3, Tra-1-60, and Tra-1-81 were also expressed. Cells with normal karyotypes were continuously maintained for more than 20 passages. The cells were capable of forming teratomas 5-7 weeks after injection into severe combined immunodeficient (SCID) mice.

E8 (TGF-β) and E8 (NODAL) supported pluripotency of every pluripotent cell line tested, i.e., two human ES cell lines (H1 and H9) and five iPSC lines for more than 25 passages (approximately 3 months) with no sign of differentiation (FIG. 3). H1 ES cells grown in E8 media have a similar gene expression profile compared to H1 ES cells grown in TeSR™ (FIG. 3B).

Example 8

Derivation of iPS Cells in Albumin-Free Media

Available reprogramming protocols include incubation of the cells in PBS in the first several days after viral transduction or electroporation, prior to switching the cells to UM100 (U.S. Pat. No. 7,439,064, incorporated herein as if set forth in its entirety) or CM. The simplified media described in previous Examples were tested for their ability to support reprogramming. ES-derived somatic cells could be reprogrammed efficiently in DF5S medium using lentivirus or episomal vectors with or without an initial 2 day culture in FBS-containing media. However, DF5S did not support reprogramming of primary foreskin cells using Nanog, Oct4, Sox2 and Lin28. DF5SFe supported reprogramming of foreskin and adult cells on Matrigel or MEFs using improved lentivirus (Ebert et al., Nature 457(7227):277-280 (2009), incorporated herein by reference as if set forth in its entirety) when the cells were initially incubated in FBS-containing medium. While DF5SFe was as effective as CM in supporting reprogramming, initial exposure to FBS appeared important for reprogramming.

Figures 4, 4C:
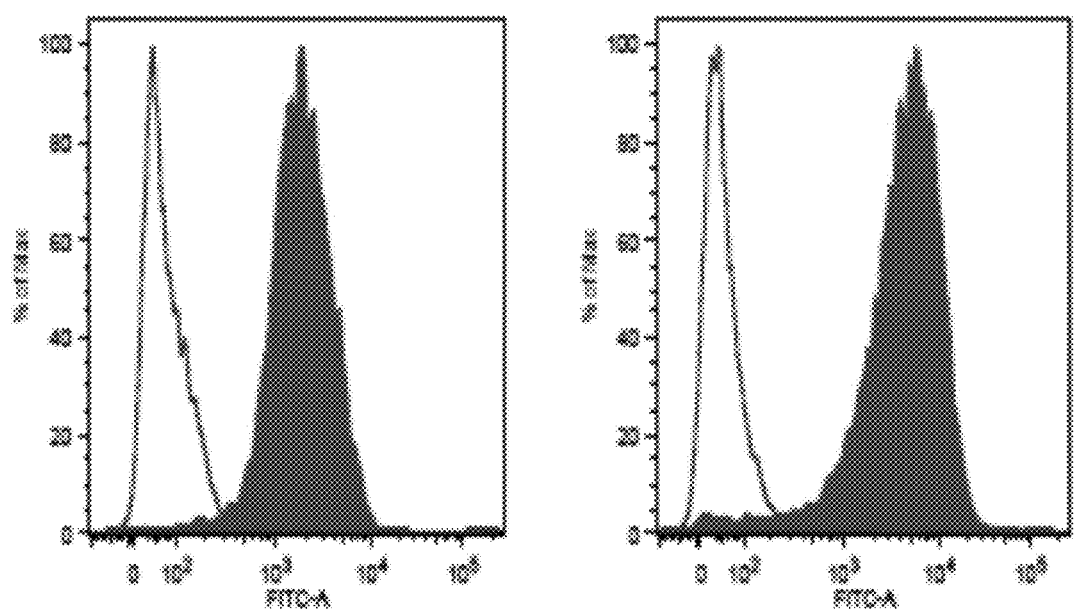

Foreskin cells grow significantly slower in DF5SFe than in FBS media. To determine growth factors that can help primary foreskin cell growth, individual growth factors contained in FBS were tested. The FGF family of growth factors has several members, one or more of which is commonly used for fibroblast culture. DF5SFe contains 100 ng/ml zebrafish recombinant FGF2. Each FGF family member was tested for its ability to support foreskin cell growth. Foreskin cells were aliquoted into the well of culture plates and incubated for 24 hours in DF5SFe minus FGF. Individual FGF types were added at 100 ng/ml for 96 h. FGF1, zFGF2, FGF4, FGF6, and FGF9 supported foreskin cell growth most effectively, but none supported cell growth as well as FBS-containing media (FIG. 4A). To identify if a non-FGF family member growth factor could promote foreskin cell growth comparable to that seen with FBS, several known fibroblast growth-promoting factors were tested. Hydrocortisone (FIG. 4B), its derivatives, and dexamethasone added to DF5SFe to replace FBS improved cell growth significantly. DF5SFe+hydrocortisone ("DF5SFeC") also improved iPS cell cloning efficiency.

To determine if DF5S-based media can be used for viral-free iPS cell derivation, foreskin cells were reprogrammed using a viral-free episomal vector, as described in Yu et al., Science 324:797 (2009), incorporated herein by reference as if set forth in its entirety, at hypoxic conditions (O5C10). Plasmid combinations #4 (pEP4EP2SCK2MEN2L and pEP4EO2SET2K, Table 3), #6 (pEP4EO2SEN2L, pEP4EO2SET2K and pEP4EO2SEM2K, Table 3), and #19 (pEP4EO2SEN2K, pEP4EO2SET2K, and pCEP4-M2L, Table 3) were used, and 2 clones were isolated from $10^6$ cells after secondary passage.

TABLE 3

Reprogramming vector components and vector combinations

| Component | Abbr. | Source | SEQ ID NO | Accession # or sequence |
|---|---|---|---|---|
| OCT4 | O | hESC | 1 | NM_002701 |
| SOX2 | S | hESC | 2 | NM_003106 |
| NANOG | N | hESC | 3 | NM_024865 |
| LIN28 | L | hESC | 4 | NM_024674 |
| c-Myc | M | hESC | 5 | NM_002467 |
| KLF4 | K | hESC | 6 | NM_004235 |
| SV40 T | T | pBABE-puro SV40 LT p | 7 | EF579667 |
| TERT | TERT | pBABE-hygro-hTERT | 8 | NM_198253 |
| IRES2 | 2 | pIRES2EGFP | 9 | — |
| CMV | C | | 10 | — |
| EF1α | E | | 11 | — |

| Vector Combinations | | |
|---|---|---|
| Combination Number | Plasmids | Components |
| 4 | pEP4EP2SCK2MEN2L | pEP4-EF1α-OCT4-IRES2-SOX2-CMV-KLF4-IRES2-c-Myc-EF1α-NANOG-IRES2-LN28 |
| | pEP4EO2SET2K | pEP4-EF1α-OCT4-IRES2-SOX2-EF1α-SV40T-IRES2-KLF4 |
| 6 | pEP4EO2SEN2L | pEP4-EF1α-OCT4-IRES2-SOX2-EF1α-NANOG-IRES2-LN28 |
| | pEP4EO2SET2K | pEP4-EF1α-OCT4-IRES2-SOX2-EF1α-SV40T-IRES2-KLF4 |
| | pEP4EO2SEM2K | pEP4-EF1α-OCT4-IRES2-SOX2-EF1α-c-Myc-IRES2-KLF4 |

TABLE 3-continued

Reprogramming vector components and vector combinations

| 19 | pEP4EO2SE N2K | pEP4-EF1α-OCT4-IRES2-SOX2-EF1α-NANOG-IRES2-KLF4 |
| | pEP4EO2SE T2K | pEP4-EF1α-OCT4-IRES2-SOX2-EF1α-SV40T-IRES2-KLF4 |
| | pCEP4-M2L | pCEP4-CMV-c-Myc-IRES2-LN28 |

Plasmid combinations #6 and #19 were used for the reprogramming. In order to enhance the plasmid entry into the nucleus, ENBA mRNA was electroporated along with plasmid DNA. Around one million cells were transferred onto two 6-well plates in DF5SFeC for 5 days. Medium was then switched to DF5SFe for another 18-25 days. Cells of some of the wells were passaged for a second time using a 1:6 ratio at different time points. Plasmid combination #19 generated more colonies than plasmid combination #6, but most of them did not resemble typical human ES cell morphology. After approximately 25 days, human ES cell-like colonies appeared on the primary plate for both plasmid combinations, with an estimated 24 reprogrammed cells per million foreskin cells using plasmid combination #19 and 8 reprogrammed cells per million foreskin cells using plasmid combination #6. The number of human ES cell-like colonies significantly increased after the secondary passage plates, with an estimated >500/million foreskin cells for each plasmid combination. The increase in the iPS cell colonies on secondary passage plates are likely due to the split of iPS cells on the primary plates. In some instances, primary plates did not have any colonies resembling typical human ES cell morphology, but many iPS cells appeared after secondary passage, suggesting that some iPS cells could not be identified, possibly because they were mixed with somatic cells.

Cells of the iPS cell colonies derived in DF5SFe started to differentiate after only two passages. Six iPS cell colonies were picked from the primary plate and transferred directly into Nodal-containing DF5SFeN (E8 (NODAL)). These cells could be maintained in E8 (Nodal) for more than 15 passages, maintaining their ES cell-like morphology similar to that observed using TeSR™. The cells had normal karyotypes, expressed Oct4 and SSEA4 (FIG. 4C), and formed teratomas in SCID mice 5-7 weeks after injection.

Figures 4, 4D:
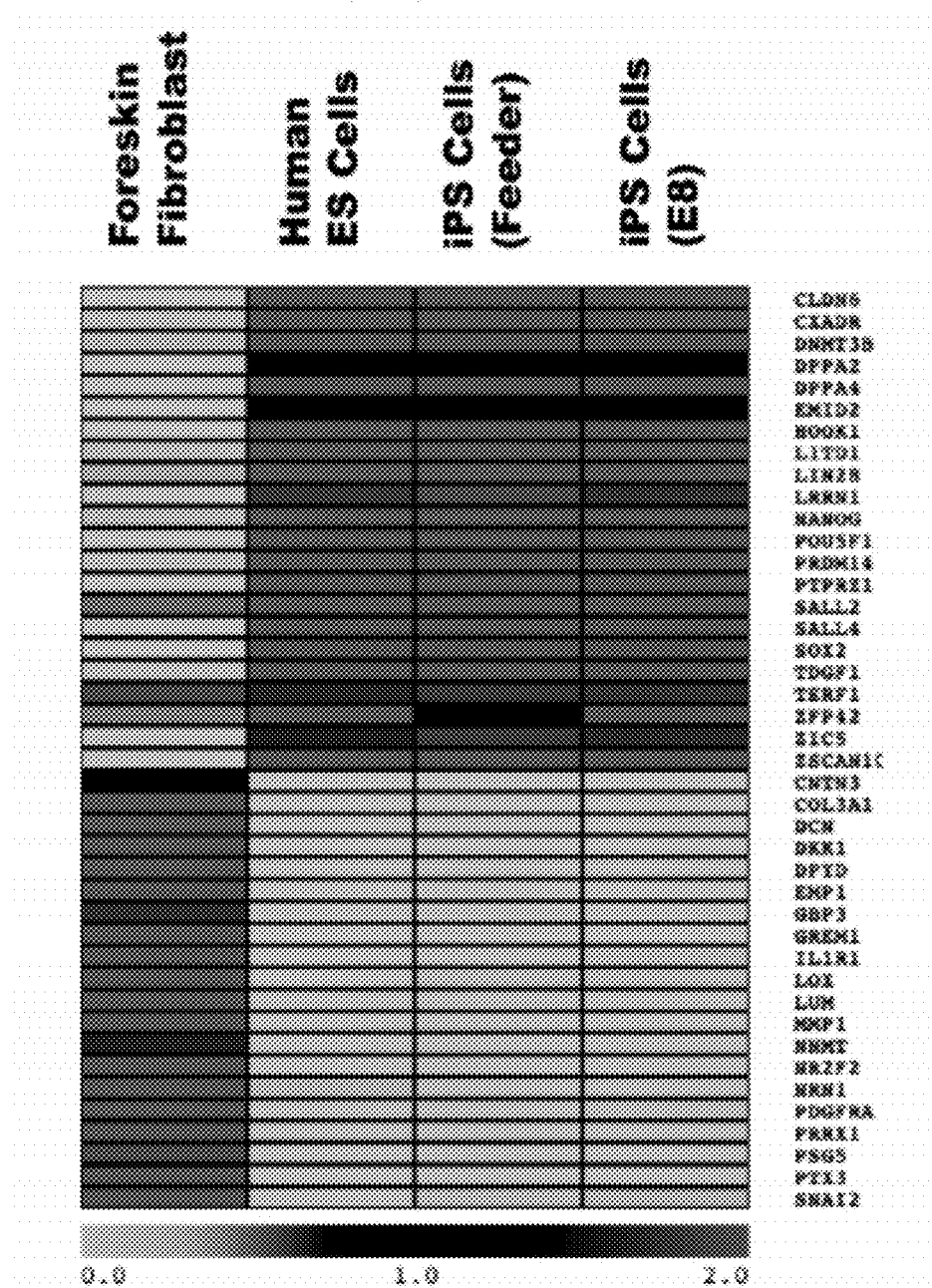

Foreskin fibroblasts were also reprogrammed in E8 medium. Global gene expression of iPS cells derived in E8 medium was similar to that of H1 cells (FIGS. 4D and E) or iPS cells derived on feeder cells (FIGS. 4D and F). Pluripotency markers were highly expressed in both ES and iPS cells, while fibroblast specific marker genes were not expressed (FIG. 4D). Also, iPS cell could be derived in E8 media using various strategies, e.g., using lentiviral or episomal vectors.

Example 9

Derivation of iPS Cells from Patient Cell Lines in Albumin-Free Media

To determine if cells from adult donors could be reprogrammed using viral-free episomal vectors in the simplified media, two million cells of the patient cell lines OAT or PRPT8 were electroporated with plasmid combinations #4 or #6, along with EBNA mRNA, and transferred onto two 10 cm plates. To maximize reprogramming, FBS-containing media was used for the first 6 days. Cells were kept at O15C5 to match regular adult cell maintenance conditions. Medium was then switched to DF5SFe for another 14-21 days. The cells of one plate were passaged at a 1:2 ratio at different time points. Plasmid combination #6 generated more colonies (approximately 5 per one million cells) than #4, but most of the cells did not resemble typical human ES cell morphology. After approximately 22 days, human ES cell-like colonies appeared on the primary plate for plasmid combination #4. Many more human ES cell-like colonies appeared on the secondary passage plates when plasmid combination #6 was used, with an estimate of approximately 40 colonies per million cells. No iPS cells were produced when using plasmid combination #4. The iPS cell colonies emerged in the middle of other densely-populated cells on the primary plate and could not grow beyond their boundary. However, colonies on the secondary plates expanded to large sizes suitable for colony isolation. Colonies were picked and directly transferred into TeSR™, and 32 picked colonies survived and displayed ES-cell morphology. Genetic analysis confirmed that these colonies were derived from the OAT cell line and exhibited a normal karyotype.

To improve adult cell reprogramming efficiency, TGF-β was added to the reprogramming media. iPS clones were not increased significantly, however, the total number of colonies increased significantly. When TGF-β was removed from the media at the time of hydrocortisone removal, the number of iPS cell colonies increased significantly, suggesting that TGF-β supports reprogramming in the first few days of the process.

Figures 5, 5C:
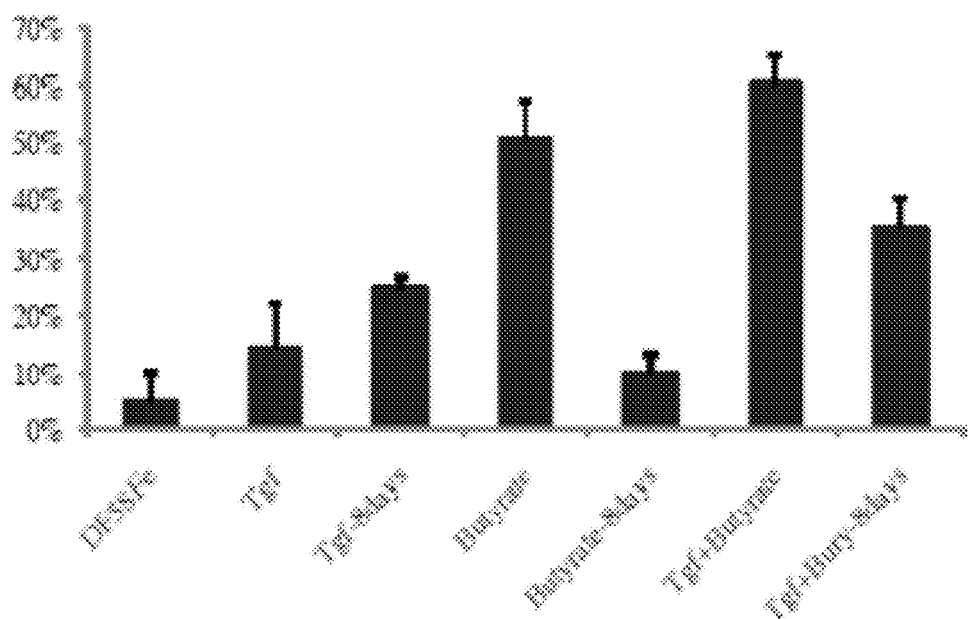

Many seemingly non-iPS clones can generate iPS clones after secondary passage, suggesting that iPS cell derivation might be inhibited by surrounding cells. Several reagents were tested for their ability to overcome this effect. Butyrate improved reprogramming efficiency. An approximately 10-fold increase in reprogramming efficiency of foreskin cells was observed when both TGF-β and butyrate were added to the media (FIG. 5B). TGF-β appeared to exhibit its positive effects during early stages of reprogramming, while butyrate had a positive role in the later stage. TGF-β addition led to increased numbers of colonies during reprogramming, but the number of true iPS cell colonies remained low. Butyrate did not increase the number of colonies, but improved the ratio of true iPS cell to non-iPS cell colonies significantly (FIG. 5C).

Using TGF-β and butyrate enabled successful reprogramming of somatic cells from an adult individual under completely defined conditions using the episomal vector system. iPS cells were derived from three independent adult somatic cell lines (OAT, GRC M1-29, and PRPF8-2) at an efficiency of 1-100 out of $1 \times 10^6$ PRPF8-2 cells and 1 out of 100,000 cells (GRC1-29).

Example 10

Derivation of iPS Cells from an Adult Individual in Completely Defined Conditions A biopsy was taken from the skin of a male adult donor, washed several times with Hank's Buffered Salt Solution (HBSS) containing antibiotics and antimycotic agents, and incubated in 2 ml of 0.25% trypsin/EDTA (Table 4) or TrypLE select at 4° C. overnight. The sample was rinsed three times, using trypsin inhibitor (Table 4) after the second rinse. The dermis and epidermis were separated using sterile forceps. The dermis was cut into small pieces and incubated in 0.75 ml enzyme solution (Table 4) with defined enzymes at room temperature (12-well or 24-well plate) for 3 hours. After approximately 35 minutes, tissue structures started to break down. An equal volume of medium with 10 μg/ml polyvinylpyrrolidone (PVP) was added and the tissue was mechanically dissociated by pipetting up and down about 10 times. The sample was centrifuged at 400 g for 10 minutes at room temperature and washed twice with fresh media/PVP. The supernatant was discarded, the pellet resuspended in 3 ml of complete medium, and 1 ml of the cell suspension was transferred into wells of 6-well plates coated with 3 μg/well vitronectin. The plates were incubated with 5% $CO_2$ at 37° C. and the medium was changed every day. Fibroblasts adhered to the plates while nonadherent cells and debris were removed when the medium was changed.

TABLE 4

Reagents and procedures for specimen digestion.

| Trypsin/EDTA | Enzyme solution | Trypsin inhibitor |
| --- | --- | --- |
| TrypZean 1x (Sigma) TrypLE animal free 0.05%~0.25% (Invitrogen) | HEPES containing RPMI supplemented with 1 mM sodium pyruvate, 1.0 mg/ml Collagenase, 150 units/ml Hyaluronidase, and 140 units/ml DNase I (Roche) | 10 mg/ml Trypsin inhibitor (from *Glycine max*) in Water or PBS |

After 20 days, reprogramming plasmids were introduced into the fibroblasts using electroporation. Within the next 25 days, multiple iPS colonies emerged and were picked for further analysis. Reprogramming efficiency was about 10 out of 1 million electroporated fibroblasts, without secondary passaging. iPS cells were further passaged to isolate vector-free cell lines.

Example 11

Derivation of iPS Cells from an Adult Individual in Albumin-Free Media Without Secondary Passage Adult fibroblasts were reprogrammed in E8 (DMEM/F12 supplemented with insulin, transferrin, selenium, L-ascorbic acid, FGF2, and TGF-β (or NODAL)) following the general protocol illustrated in FIG. 6A. Reprogrammed iPS cell lines maintained in E8 for more than 20 passages continued to express pluripotency markers OCT4 and SSEA4 (FIG. 6B).

Figures 7, 7C:
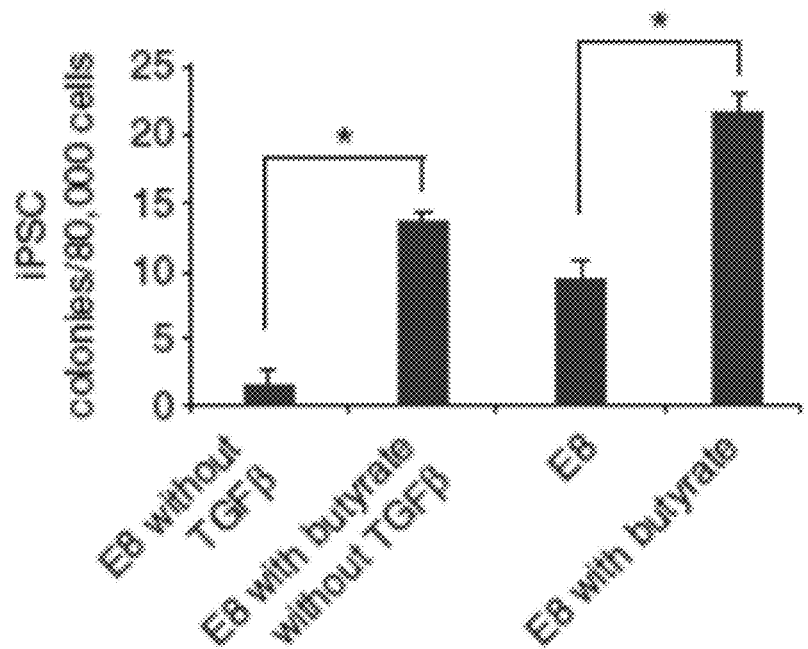

E8 medium significantly enhanced reprogramming efficiency compared to reprogramming efficiencies using mouse fibroblast feeder cells (MEF) (FIG. 7A) or TeSR™ (FIG. 7B). Butyrate (100 μM) further enhanced reprogramming efficiency in the presence of TGF-β (E8) or in the absence of TGF-β (E8 without of TGF-β, i.e., DF5SFe) (FIG. 7C).

Example 12

Cryopreservation of Pluripotent Stem Cells in an Albumin-Free Media

Pluripotent cells were cultured in 6-well plates in E8 medium, essentially as described above. The culture medium was aspirated from each well and the cells were washed twice with 1.0 mL EDTA/PBS (0.5 mM EDTA in PBS, osmalority 340). The cells were then incubated at 37° C. in EDTA/PBS for 5 minutes. The PBS/EDTA was removed, and the cells were rinsed swiftly with 1 ml of E8 medium. The cells were then resuspended in an equal volume of 20% dimethyl sulfoxide (DMSO) and E8 medium (final concentration: 10% DMSO in E8 medium), aliquoted into cryogenic vials, and frozen at −80° C. using a CRYOBOX™. The cells were subsequently moved into a liquid nitrogen tank.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A defined, albumin-free medium free of any component obtained from a non-human animal, the medium comprising water, salts, amino acids, vitamins, glucose, insulin, an FGF, selenium, transferrin, and one of TGF-β and NODAL, each in an amount sufficient to support human pluripotent stem cell proliferation.

2. A method for culturing human pluripotent stem cells, the method comprising the steps of:
    placing pluripotent stem cells on a matrix; and
    contacting the cells with a defined, albumin-free medium free of any component obtained from a non-human animal, the medium comprising water, salts, amino acids, vitamins, glucose, insulin, an FGF, selenium, transferrin, and one of TGF-β and NODAL, each in an amount sufficient to support human pluripotent stem cell proliferation.

3. The method of claim 2, wherein the matrix comprises laminin.

4. The method of claim 2, wherein the matrix comprises vitronectin.

5. The method of claim 2, wherein the cells are contacted with the medium under hypoxic conditions.

6. The method of claim 2, wherein the pluripotent stem cells are embryonic stem cells.

7. The method of claim 2, wherein the pluripotent stem cells are induced pluripotent stem cells.

8. A method for cloning a human pluripotent stem cell, the method comprising the step of:
    plating human pluripotent stem cells at cloning density in a defined albumin-free medium free of any component obtained from a non-human animal, the medium comprising water, salts, amino acids, vitamins, glucose, insulin, an FGF, selenium, transferrin, and one of TGF-β and NODAL, each in an amount sufficient to support human pluripotent stem cell cloning.

9. The method of claim 8, wherein the medium further comprises a ROCK inhibitor.

10. The method of claim 9, wherein the ROCK inhibitor is selected from the group consisting of HA100 and Y27632.

11. The method of claim 8, wherein the medium further comprises blebbistatin.

12. A method of cryopreserving human pluripotent stem cells, the method comprising the step of:
    freezing human pluripotent stem cells in a defined, albumin-free medium free of any component obtained from a non-human animal, the medium comprising water, salts, amino acids, vitamins, glucose, insulin, an FGF, selenium, transferrin, and one of TGF-β and NODAL, each in an amount sufficient to support human pluripotent stem cell proliferation.

13. The defined, albumin-free medium of claim 1, consisting essentially of: water, salts, amino acids, vitamins, glucose, insulin, an FGF, selenium, transferrin, and one of TGF-β and NODAL.

14. The defined, albumin-free medium of claim 1, wherein the medium comprises TGF-β.

15. The defined, albumin-free medium of claim 1, wherein the medium comprises NODAL.

16. The defined, albumin-free medium of claim 1, further comprising a ROCK inhibitor.

17. The defined, albumin-free medium of claim 16, wherein the ROCK inhibitor is selected from the group consisting of HA100 and Y27632.

18. The defined, albumin-free medium of claim 1, further comprising blebbistatin.

19. The defined, albumin-free medium of claim 1, consisting of: water, salts, amino acids, vitamins, glucose, insulin, an FGF, selenium, transferrin, and one of TGF-β and NODAL.

* * * * *

UNITED STATES PATENT AND TRADEMARK OFFICE
CERTIFICATE OF CORRECTION

Page 1 of 1

PATENT NO. : 9,279,103 B2
APPLICATION NO. : 13/204354
DATED : March 8, 2016
INVENTOR(S) : Guokai Chen and James A. Thomson It is certified that error appears in the above-identified patent and that said Letters Patent is hereby corrected as shown below:

In the Specification
Column 13, line 55 - "PBS" should be --FBS--

Signed and Sealed this
Twenty-first Day of June, 2016

Michelle K. Lee
*Director of the United States Patent and Trademark Office*